(12) United States Patent
Kane et al.

(10) Patent No.: US 7,879,012 B2
(45) Date of Patent: Feb. 1, 2011

(54) MEDICAL VALVE WITH RESILIENT SEALING MEMBER

(75) Inventors: Jeffrey F. Kane, Hudson, MA (US); Ian Kimball, Clinton, MA (US); Todd S. Vangness, Stow, MA (US)

(73) Assignee: Nypro Inc., Clinton, MA (US)

( * ) Notice: Subject to any disclaimer, the term of this patent is extended or adjusted under 35 U.S.C. 154(b) by 419 days.

(21) Appl. No.: 11/786,457

(22) Filed: Apr. 11, 2007

(65) Prior Publication Data

US 2007/0255229 A1 Nov. 1, 2007

Related U.S. Application Data

(60) Provisional application No. 60/790,914, filed on Apr. 11, 2006, provisional application No. 60/837,442, filed on Aug. 11, 2006, provisional application No. 60/883,674, filed on Jan. 5, 2007.

(51) Int. Cl.
*A61M 5/178* (2006.01)
(52) U.S. Cl. .................. 604/167.03; 604/248
(58) Field of Classification Search ............. 604/248, 604/167.03, 167.05, 167.16
See application file for complete search history.

(56) References Cited

U.S. PATENT DOCUMENTS

| | | | |
|---|---|---|---|
| 2,705,501 A | 4/1955 | Frizsch et al. ............. 137/113 |
| 2,919,935 A | 1/1960 | Nyberg ...................... 284/18 |
| 3,087,492 A | 4/1963 | Garth ......................... 128/350 |
| 3,192,949 A | 7/1965 | DeSee ........................ 137/540 |
| 3,279,497 A | 10/1966 | Norton et al. .......... 137/614.03 |
| 3,385,301 A | 5/1968 | Harautuneian ............ 128/349 |
| 3,399,677 A | 9/1968 | Gould et al. ............... 128/349 |
| 3,423,063 A | 1/1969 | German ................... 251/149.6 |
| 3,618,892 A | 11/1971 | Scioto ..................... 251/149.2 |
| 3,806,086 A | 4/1974 | Cloyd ..................... 251/149.7 |

(Continued)

FOREIGN PATENT DOCUMENTS

EP 0 629 418 A2 12/1994

(Continued)

OTHER PUBLICATIONS

US 6,971,630, 12/2005, Leinsing et al. (withdrawn)

*Primary Examiner*—Kevin C Sirmons
*Assistant Examiner*—Deanna K Hall
(74) *Attorney, Agent, or Firm*—Sunstein Kann Murphy & Timbers LLP

(57) ABSTRACT

A medical valve transitions between an open mode that permits fluid flow, and a closed mode that prevents fluid flow. To that end, the valve has a housing with an inlet and an outlet, and a movable member with a member channel therethrough. The movable member is movable to cause the valve to transition from the closed mode to the open mode after insertion of a medical implement into the inlet. The member channel fluidly communicates the inlet and the outlet when in the open mode. The valve also has a resilient member with a member flow path in fluid communication with the outlet. The movable member slides along the resilient member when transitioning between the open mode and the closed mode. The resilient member normally has a flange (about the member flow path) that is compressed by the movable member. The flange fluidly disconnects the member flow path from the member channel when in the closed mode.

27 Claims, 19 Drawing Sheets

U.S. PATENT DOCUMENTS

| | | | |
|---|---|---|---|
| 3,831,629 A | 8/1974 | Mackal et al. | 137/525 |
| 3,838,843 A | 10/1974 | Bernhard | 251/149.1 |
| 3,921,656 A | 11/1975 | Meisenheimer, Jr. et al. | 137/68 |
| 3,923,065 A | 12/1975 | Nozick et al. | 128/348 |
| 3,965,910 A | 6/1976 | Fischer | 128/349 R |
| 4,063,555 A | 12/1977 | Ulinder | 128/214 R |
| 4,080,965 A | 3/1978 | Phillips | 128/214 D |
| 4,116,201 A | 9/1978 | Shah | 128/351 |
| 4,143,853 A | 3/1979 | Abramson | 251/149.1 |
| 4,181,149 A | 1/1980 | Cox | 137/614.02 |
| 4,223,808 A | 9/1980 | Williams et al. | 222/88 |
| 4,324,239 A | 4/1982 | Gordon et al. | 128/214 R |
| 4,335,747 A | 6/1982 | Mitsumoto et al. | 137/614.06 |
| 4,344,435 A | 8/1982 | Aubin | 128/350 R |
| 4,421,296 A | 12/1983 | Stephens | 251/149.7 |
| 4,445,664 A | 5/1984 | Allread | 251/149.2 |
| 4,473,211 A | 9/1984 | Fremy | 251/149.2 |
| 4,496,348 A | 1/1985 | Genese et al. | 604/167 |
| 4,535,820 A | 8/1985 | Raines | 137/854 |
| 4,627,598 A | 12/1986 | Fremy | 251/149.2 |
| 4,664,149 A | 5/1987 | Fremy | 137/614.06 |
| 4,675,003 A | 6/1987 | Hooven | 604/9 |
| 4,683,905 A | 8/1987 | Vigneau et al. | 137/329 |
| 4,683,916 A | 8/1987 | Raines | 137/854 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/249 |
| 4,745,950 A | 5/1988 | Mathieu | 137/798 |
| 4,752,287 A | 6/1988 | Kurtz et al. | 604/99 |
| 4,809,679 A | 3/1989 | Shimonaka et al. | 128/4 |
| 4,819,684 A | 4/1989 | Zaugg et al. | 137/112 |
| 4,905,965 A | 3/1990 | Dolev | 251/149.9 |
| 4,915,687 A | 4/1990 | Sivert | 604/83 |
| 4,917,668 A | 4/1990 | Haindl | 604/249 |
| 4,944,329 A | 7/1990 | Cardin et al. | 137/614.05 |
| 5,006,114 A | 4/1991 | Rogers et al. | 604/167 |
| 5,041,087 A | 8/1991 | Loo et al. | 604/83 |
| 5,049,128 A | 9/1991 | Duquette | 504/83 |
| 5,050,841 A | 9/1991 | Jacobsson | 251/149.9 |
| 5,080,654 A | 1/1992 | Picha et al. | 604/167 |
| 5,085,645 A | 2/1992 | Purdy et al. | 604/167 |
| 5,098,394 A | 3/1992 | Luther | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,171,230 A | 12/1992 | Eland et al. | 604/250 |
| 5,184,652 A | 2/1993 | Fan | 141/21 |
| 5,203,775 A | 4/1993 | Frank et al. | 604/256 |
| 5,215,538 A | 6/1993 | Larkin | 604/249 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,295,657 A | 3/1994 | Atkinson | 251/149.1 |
| 5,300,034 A | 4/1994 | Behnke et al. | 604/167 |
| 5,330,435 A | 7/1994 | Vaillancourt | 604/167 |
| 5,342,326 A | 8/1994 | Peppel et al. | 604/284 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,397,314 A | 3/1995 | Farley et al. | 604/256 |
| 5,401,255 A | 3/1995 | Sutherland et al. | 604/247 |
| 5,403,284 A | 4/1995 | Gross | 604/167 |
| 5,439,451 A | 8/1995 | Collinson et al. | 604/247 |
| 5,458,640 A | 10/1995 | Gerrone | 604/264 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,489,274 A | 2/1996 | Chu et al. | 604/167 |
| 5,509,433 A | 4/1996 | Paradis | 137/1 |
| 5,509,912 A | 4/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,540,661 A | 7/1996 | Tomisaka et al. | 604/265 |
| 5,549,566 A | 8/1996 | Elias et al. | 604/167 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,782,816 A | 7/1998 | Werschmidt et al. | 604/256 |
| 5,806,831 A | 9/1998 | Paradis | 251/149.1 |
| 5,820,601 A | 10/1998 | Mayer | 604/167 |
| 5,836,923 A | 11/1998 | Mayer | 604/246 |
| 5,921,264 A | 7/1999 | Paradis | 137/15 |
| 5,947,954 A | 9/1999 | Bonaldo | 604/533 |
| 5,957,898 A | 9/1999 | Jepson et al. | 604/256 |
| 6,029,946 A | 2/2000 | Doyle | 251/149.1 |
| 6,036,171 A | 3/2000 | Weinheimer et al. | 251/149.1 |
| 6,039,302 A | 3/2000 | Cote, Sr. et al. | 251/149.1 |
| 6,048,335 A | 4/2000 | Mayer | 604/167 |
| 6,050,978 A | 4/2000 | Orr et al. | 604/249 |
| 6,063,062 A | 5/2000 | Paradis | 604/249 |
| 6,068,011 A | 5/2000 | Paradis | 137/1 |
| 6,079,432 A | 6/2000 | Paradis | 137/1 |
| 6,089,539 A | 7/2000 | Kouda | 251/149.2 |
| 6,089,541 A | 7/2000 | Weinheimer et al. | 251/149.6 |
| 6,090,074 A | 7/2000 | Brimhall et al. | 604/167.05 |
| 6,117,114 A | 9/2000 | Paradis | 604/246 |
| 6,142,446 A | 11/2000 | Leinsing | 251/149.1 |
| 6,152,900 A | 11/2000 | Mayer | 604/167 |
| 6,183,448 B1 | 2/2001 | Mayer | 604/256 |
| 6,206,860 B1 | 3/2001 | Richmond | 604/246 |
| 6,206,861 B1 | 3/2001 | Mayer | 604/246 |
| 6,228,069 B1 | 5/2001 | Barth et al. | 604/249 |
| 6,245,048 B1 | 6/2001 | Fangrow, Jr. et al. | 604/249 |
| 6,290,206 B1 | 9/2001 | Doyle | 251/149.1 |
| 6,344,033 B1 | 2/2002 | Jepson et al. | 604/256 |
| 6,364,869 B1 | 4/2002 | Bonaldo | 604/537 |
| 6,422,267 B1 | 7/2002 | Makishima et al. | 137/616.7 |
| 6,428,520 B1 | 8/2002 | Lopez et al. | 604/249 |
| 6,485,472 B1 | 11/2002 | Richmond | 604/246 |
| 6,491,668 B1 | 12/2002 | Paradis | 604/246 |
| 6,541,802 B2 | 4/2003 | Doyle | 257/149.1 |
| 6,543,745 B1 | 4/2003 | Enerson | 251/149.7 |
| 6,595,964 B2 | 7/2003 | Finley et al. | 604/246 |
| 6,595,981 B2 | 7/2003 | Huet | 604/523 |
| 6,598,620 B1 | 7/2003 | Fremy | 137/614.03 |
| 6,609,696 B2 | 8/2003 | Enerson | 251/86 |
| 6,669,673 B2 | 12/2003 | Lopez | 604/249 |
| 6,695,817 B1 | 2/2004 | Fangrow, Jr. | 604/167.01 |
| 6,706,022 B1 | 3/2004 | Leinsing et al. | 604/247 |
| 6,755,391 B2 | 6/2004 | Newton et al. | 251/149.6 |
| 6,779,777 B2 | 8/2004 | Kouda | 251/149.6 |
| 6,802,490 B2 | 10/2004 | Leinsing et al. | 251/149.6 |
| 6,811,139 B2 | 11/2004 | Hishikawa | 251/149.1 |
| 6,827,329 B2 | 12/2004 | Mikiya et al. | 251/97 |
| 6,840,501 B2 | 1/2005 | Doyle | 251/149.1 |
| 6,869,426 B2 | 3/2005 | Ganem | 604/533 |
| 6,883,778 B1 | 4/2005 | Newton et al. | 251/149.1 |
| 6,899,132 B2 * | 5/2005 | Mikiya et al. | 137/616.7 |
| 6,916,309 B2 | 7/2005 | Fangrow, Jr. | 604/167.01 |

| | | | | | | |
|---|---|---|---|---|---|---|
| 6,932,795 B2 | 8/2005 | Lopez et al. ............... 604/249 | | 2006/0200072 A1 | 9/2006 | Peppel .................... 604/93.01 |
| 6,964,406 B2 | 11/2005 | Doyle .................... 251/149.6 | | 2006/0200088 A1 | 9/2006 | Lopez et al. ............... 604/246 |
| 6,991,215 B2 | 1/2006 | Kiehne ................... 251/149.6 | | 2006/0200089 A1 | 9/2006 | Lopez et al. ............... 604/246 |
| 7,004,934 B2 | 2/2006 | Vaillancourt ............... 604/533 | | 2006/0200090 A1 | 9/2006 | Lopez et al. ............... 604/246 |
| 7,014,169 B2 | 3/2006 | Newton et al. ........... 251/149.6 | | 2006/0206061 A1 | 9/2006 | Lopez et al. ............... 604/246 |
| 7,028,982 B2 | 4/2006 | Kohda .................... 251/149.2 | | 2006/0211997 A1 | 9/2006 | Fangrow .................... 604/246 |
| 7,037,302 B2 | 5/2006 | Vaillancourt ............... 604/533 | | 2006/0211998 A1 | 9/2006 | Fangrow .................... 604/246 |
| 7,056,308 B2 | 6/2006 | Utterberg ................... 604/256 | | 2006/0211999 A1 | 9/2006 | Fangrow .................... 604/246 |
| 7,063,685 B2 | 6/2006 | Rome ........................ 604/246 | | 2006/0217671 A1 | 9/2006 | Peppel ...................... 604/246 |
| 7,070,164 B2 | 7/2006 | Kohda .................... 251/149.2 | | 2006/0264848 A1 | 11/2006 | Fangrow .................... 604/249 |
| 7,104,520 B2 | 9/2006 | Leinsing et al. .......... 251/149.6 | | 2006/0264849 A1 | 11/2006 | Lopez et al. ............... 604/249 |
| 7,114,701 B2 | 10/2006 | Peppel ....................... 251/149 | | 2006/0270999 A1 | 11/2006 | Fangrow .................... 604/249 |
| 7,118,560 B2 | 10/2006 | Bonaldo .................... 604/537 | | 2006/0271016 A1 | 11/2006 | Fangrow .................... 604/539 |
| 7,125,396 B2 | 10/2006 | Leinsing et al. ........ 604/167.03 | | 2006/0293629 A1 | 12/2006 | Cote, Sr. et al. ............. 604/246 |
| 7,131,458 B2 | 11/2006 | Kohda .................. 137/614.03 | | 2007/0100284 A1 | 5/2007 | Leinsing et al. ........ 604/164.01 |
| 7,184,825 B2 | 2/2007 | Leinsing et al. ................ 604/20 | | 2007/0112312 A1 | 5/2007 | Fangrow .................... 604/246 |
| 7,244,249 B2 | 7/2007 | Leinsing et al. ............ 604/500 | | 2007/0112313 A1 | 5/2007 | Fangrow .................... 604/246 |
| 7,306,199 B2 | 12/2007 | Leinsing et al. ......... 251/149.6 | | 2007/0235674 A1 | 10/2007 | Vangsness et al. ....... 251/149.2 |
| 7,314,061 B2 | 1/2008 | Peppel ....................... 137/605 | | 2007/0235675 A1 | 10/2007 | Kimball et al. ........... 251/149.2 |
| 7,329,249 B2 | 2/2008 | Bonaldo .................... 604/537 | | 2007/0235676 A1 | 10/2007 | Vangsness et al. ....... 251/149.2 |
| 7,343,931 B2 | 3/2008 | Packham ............... 137/614.04 | | 2007/0238337 A1 | 10/2007 | Kimball et al. ............. 439/157 |
| 7,357,792 B2 | 4/2008 | Newton et al. ............. 604/244 | | 2007/0246674 A1 | 10/2007 | Kiehne ................... 251/149.6 |
| 7,396,348 B2 | 7/2008 | Newton et al. ............. 604/256 | | 2007/0255229 A1 | 11/2007 | Kane et al. .................. 604/248 |
| 7,497,848 B2 | 3/2009 | Leinsing et al. ............ 604/247 | | 2007/0260195 A1 | 11/2007 | Bartholomew et al. ...... 604/244 |
| 7,497,849 B2 | 3/2009 | Fangrow, Jr. ................ 604/247 | | 2007/0270756 A1 | 11/2007 | Peppel et al. ........... 604/167.06 |
| 7,510,545 B2 | 3/2009 | Peppel ....................... 604/256 | | 2008/0027398 A1 | 1/2008 | McKinnon et al. ........... 604/264 |
| 2003/0050610 A1 | 3/2003 | Newton et al. ............. 604/256 | | 2008/0027415 A1 | 1/2008 | Isaacson et al. ............. 604/539 |
| 2003/0093061 A1 | 5/2003 | Ganem ...................... 604/533 | | 2008/0039802 A1 | 2/2008 | Vangsness et al. ........... 604/247 |
| 2003/0098430 A1 | 5/2003 | Leinsing et al. .......... 251/149.6 | | 2008/0172003 A1 | 7/2008 | Plishka et al. ............... 604/249 |
| 2003/0141477 A1 | 7/2003 | Miller .................... 251/149.1 | | 2008/0172005 A1 | 7/2008 | Jepson ........................ 604/249 |
| 2004/0006330 A1 | 1/2004 | Fangrow, Jr. ................ 604/533 | | 2008/0190485 A1 | 8/2008 | Guala ............................. 137/1 |
| 2004/0073171 A1 | 4/2004 | Rogers et al. .......... 604/164.13 | | 2008/0275405 A1 | 11/2008 | Newton et al. ............. 604/256 |
| 2004/0124388 A1 | 7/2004 | Kiehne .................... 251/149.1 | | 2009/0057589 A1 | 3/2009 | Thorne, Jr. et al. ........ 251/149.1 |
| 2005/0038397 A1 | 2/2005 | Newton et al. ............. 604/249 | | | | |
| 2005/0087239 A1 | 4/2005 | Kohda .................. 137/614.03 | | FOREIGN PATENT DOCUMENTS | | |
| 2005/0087241 A1 | 4/2005 | Kohda .................. 137/614.03 | | WO | WO 83/02559 | 8/1983 |
| 2005/0090805 A1 | 4/2005 | Shaw et al. ................. 604/523 | | WO | WO 97/39791 | 10/1997 |
| 2005/0121638 A1 | 6/2005 | Doyle ........................ 251/149 | | WO | WO 98/22178 | 5/1998 |
| 2005/0165365 A1 | 7/2005 | Newton et al. ............. 604/246 | | WO | WO 98/26835 | 6/1998 |
| 2005/0222541 A1 | 10/2005 | Lopez et al. ............... 604/249 | | WO | WO 98/39594 | 9/1998 |
| 2005/0228362 A1 | 10/2005 | Vaillancourt ............... 604/533 | | WO | WO 00/44433 | 8/2000 |
| 2005/0256457 A1 | 11/2005 | Rome ..................... 604/167.06 | | WO | WO 03/018104 A2 | 3/2003 |
| 2006/0108555 A1 | 5/2006 | Kiehne ................... 251/149.7 | | WO | WO 03/018105 A1 | 3/2003 |
| 2006/0129109 A1 | 6/2006 | Shaw et al. ................. 604/246 | | WO | WO 2004/006046 | 1/2004 |
| 2006/0161115 A1 | 7/2006 | Fangrow .................... 604/249 | | | | |
| 2006/0178645 A1 | 8/2006 | Peppel ....................... 604/249 | | * cited by examiner | | |

MEDICAL VALVE WITH RESILIENT SEALING MEMBER

PRIORITY

This patent application claims priority from provisional United States patent applications:

Application No. 60/790,914, filed Apr. 11, 2006, entitled, "ROTATIONAL MEDICAL VALVE," and naming Todd S. Vangsness and Jeffrey F. Kane as inventors, the disclosure of which is incorporated herein, in its entirety, by reference.

Application No. 60/837,442, filed Aug. 11, 2006, entitled, "ROTATIONAL MEDICAL VALVE," and naming Todd S. Vangsness and Jeffrey F. Kane as inventors, the disclosure of which is incorporated herein, in its entirety, by reference.

Application No. 60/883,674, filed Jan. 5, 2007, entitled, "ROTATIONAL MEDICAL VALVE," and naming Jeffrey F. Kane, Todd S. Vangsness, and Ian Kimball as inventors, the disclosure of which is incorporated herein, in its entirety, by reference.

RELATED UNITED STATES PATENT APPLICATIONS

This patent application is related to the following co-pending U.S. patent applications:

U.S. patent application Ser. No. 11/786,413, entitled, "MEDICAL VALVE WITH ROTATING MEMBER AND METHOD," naming Todd S. Vangsness, Jeffrey F. Kane, and Ian Kimball as inventors, filed on even date herewith, and the disclosure of which is incorporated herein, in its entirety, by reference.

U.S. patent application Ser. No. 11/786,437, entitled, "MEDICAL VALVE WITH RESILIENT BIASING MEMBER," naming Ian Kimball, Todd S. Vangsness, and Jeffrey F. Kane as inventors, filed on even date herewith, and the disclosure of which is incorporated herein, in its entirety, by reference.

U.S. patent application Ser. No. 11/786,425, entitled, "MEDICAL VALVE WITH MOVABLE MEMBER," naming Ian Kimball, Todd S. Vangsness, and Jeffrey F. Kane as inventors, filed on even date herewith, and the disclosure of which is incorporated herein, in its entirety, by reference.

U.S. patent application Ser. No. 11/786,452, entitled, "ANTI-DRAWBACK MEDICAL VALVE AND METHOD," naming Todd S. Vangsness, Jeffery F. Kane, and Ian Kimball as inventors, filed on even date herewith, and the disclosure of which is incorporated herein, in its entirety, by reference.

FIELD OF THE INVENTION

The invention generally relates to medical valves and, more particularly, the invention relates to resilient sealing mechanisms within a medical valve.

BACKGROUND OF THE INVENTION

In general terms, medical valving devices often act as a sealed port that may be repeatedly accessed to non-invasively inject fluid into (or withdraw fluid from) a patient's vasculature. During use, medical personnel may insert a syringe into the proximal port of a properly secured medical valve to inject fluid into (or withdraw fluid from) a patient. Once inserted, the syringe may freely inject or withdraw fluid to and from the patient.

SUMMARY OF THE INVENTION

In accordance with one embodiment of the invention, a medical valve transitions between an open mode that permits fluid flow, and a closed mode that prevents fluid flow. To that end, the valve has a housing with an inlet and an outlet, and a movable member with a member channel therethrough. The movable member is movable to cause the valve to transition from the closed mode to the open mode after insertion of a medical implement into the inlet. The member channel fluidly communicates the inlet and the outlet when in the open mode. The valve also has a resilient member with a member flow path in fluid communication with the outlet. The movable member slides along the resilient member when transitioning between the open mode and the closed mode. The resilient member normally has a flange (about the member flow path) that is compressed by the movable member. The flange fluidly disconnects the member flow path from the member channel when in the closed mode.

The member channel may have a distal opening, and the flange may be positioned generally about the distal opening when in the open mode. The flange may generally seal about the distal opening when in the open mode. Moreover, the flange may overhang the member flow path.

The movable member may compress the flange to have a surface with a contour that generally is complimentary with the contour of the portion of the movable member contacting the flange. In addition, the flange may wipe against the movable member to effectively form a wiper seal. In some embodiments, the movable member compresses the flange the entire time the valve transitions between the open and closed modes.

Among other things, the movable member is a rotational member. Moreover, the resilient member may include silicone. In some embodiments, the member channel has a distal opening and the valve has a partially open mode. In that case, the distal opening may be between first and second portions of the flange when in the partially open mode, and the first portion extends across the distal opening when in the partially open mode. The second portion of the flange is radially outward of the distal opening when in the partially open mode.

In accordance with another embodiment of the invention, a medical valve has a housing with an inlet and an outlet, and a movable member with a member channel therethrough. The movable member is movable to cause the valve to transition from the closed mode to the open mode after insertion of a medical implement into the inlet. The member channel fluidly communicates the inlet and the outlet when in the open mode. The valve also has a resilient member with a member flow path having a proximal opening. The resilient member also has a flange about the proximal opening of the member flow path, and the flange seals the proximal opening in the closed mode.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a medical valve has an internal valve mechanism with a resilient member that biases a movable member toward a closed mode. The resilient member has a flange that normally is positioned about the member flow path. The movable member compresses the flange, which fluidly disconnects portions of the flow path through the valve when in the closed mode. In addition, in some embodiments, the flange seals the flow path through the valve when in the open mode. Details of illustrative embodiments are discussed below.

Figure 1:
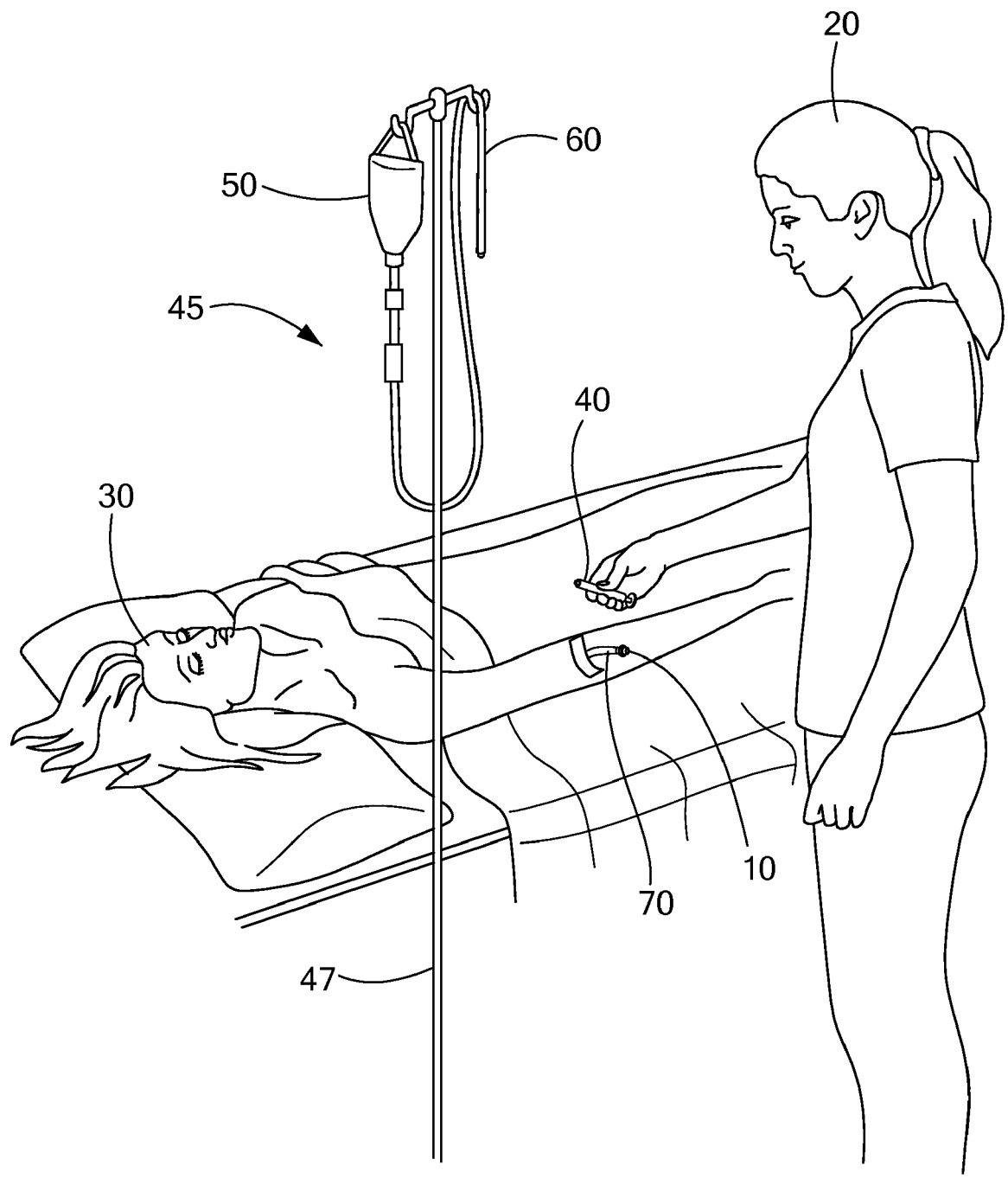
FIG. 1 schematically shows one use of a medical valve configured in accordance with one embodiment of the present invention.

FIG. 1 schematically shows one illustrative use of a medical valve 10 configured in accordance with illustrative embodiments of the invention. In this example, a catheter 70 connects the valve 10 with a patient's vein (the patient is identified by reference number 30). Adhesive tape or similar material may be coupled with the catheter 70 and patient's arm to ensure that the valve remains in place.

After the valve 10 is in place, a nurse, doctor, technician, practitioner, or other user (schematically identified by reference number 20) may intravenously deliver medication to the patient 30, who is lying in a hospital bed. To that end, after the valve is properly primed and flushed (e.g., with a saline flush), the nurse 20 swabs the top surface of the valve 10 to remove contaminants. Next, the nurse 20 uses a medical instrument (e.g., a syringe having a distally located blunt, luer tip complying with ANSI/ISO standards) to inject medication into the patient 30 through the valve 10. For example, the medical practitioner 20 may use the valve 10 to inject drugs such as heparin, antibiotic, pain medication, other intravenous medication, or other fluid deemed medically appropriate. Alternatively, the nurse 20 (or other user) may withdraw blood from the patient 30 through the valve 10.

The medical valve 10 may receive medication or other fluids from other means, such as through a gravity feed system 45. In general, traditional gravity feeding systems 45 often have a bag 50 (or bottle) containing a fluid (e.g., anesthesia medication) to be introduced into the patient 30 hanging from a pole 47. The medical practitioner 20 then connects the bag/bottle 50 to the medical valve 10 using tubing 60 having an attached blunt tip. In illustrative embodiments, the blunt tip of the tubing has a luer taper that complies with the ANSI/ISO standard. After the tubing 60 is connected to the medical valve 10, gravity (or a pump) causes the fluid to begin flowing into the patient 30. In some embodiments, the feeding system 45 may include additional shut-off valves on the tubing 60 (e.g., stop-cock valves or clamps) to stop fluid flow without having to disconnect the tubing 60 from the valve 10. Accordingly, the valve 10 can be used in long-term "indwell" procedures.

After administering or withdrawing fluid from the patient 30, the nurse 20 should appropriately swab and flush the valve 10 and catheter 70 to remove contaminants and ensure proper operation. As known by those skilled in the art, there is a generally accepted valve swabbing and flushing protocol that should mitigate the likelihood of infection. Among other things, as summarized above, this protocol requires proper flushing and swabbing before and after the valve is used to deliver fluid to, or withdraw fluid from the patient.

Figure 2A:
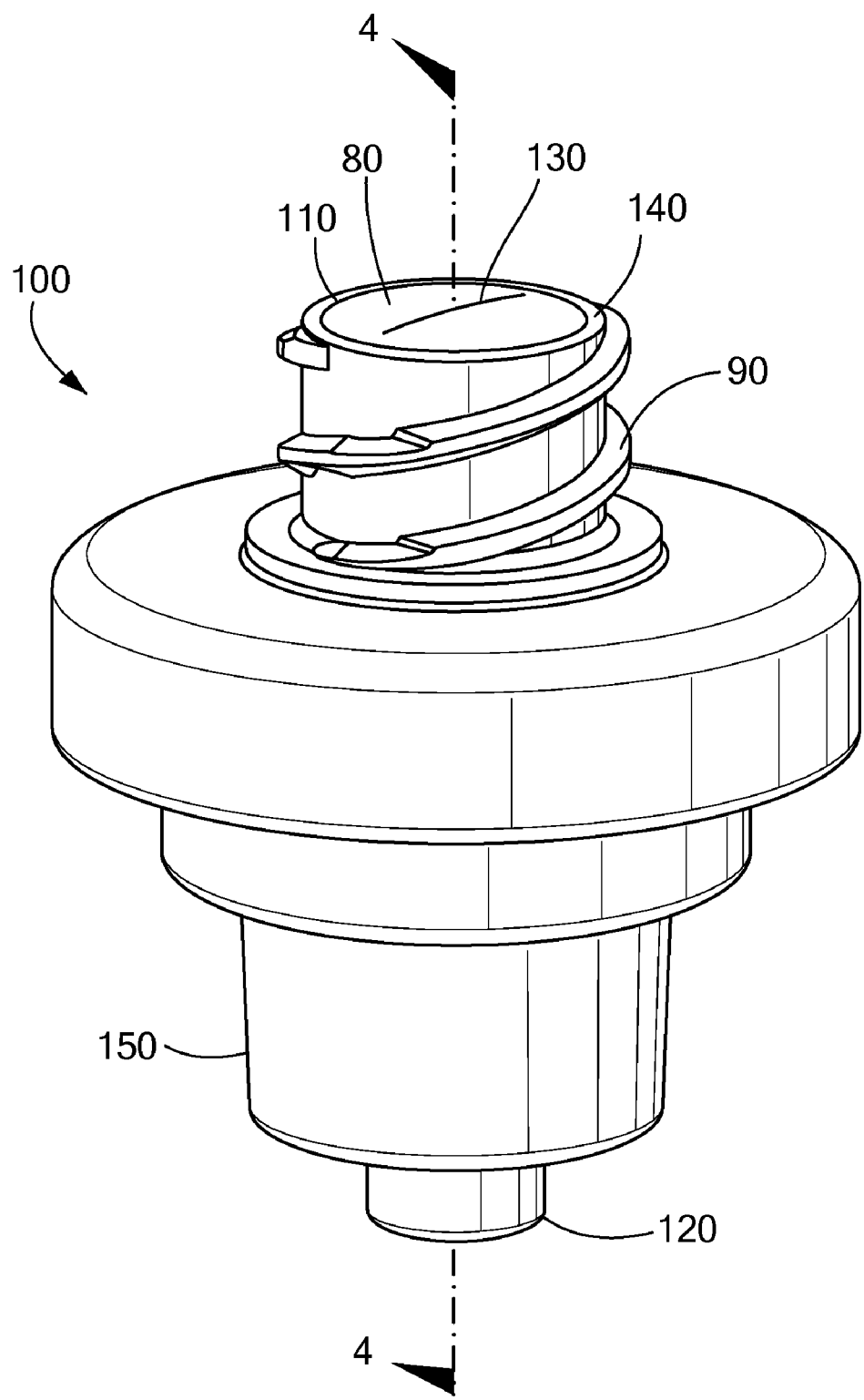
FIG. 2A schematically shows a perspective view of a medical valve configured in accordance with illustrative embodiments of the present invention.
Figure 2B:
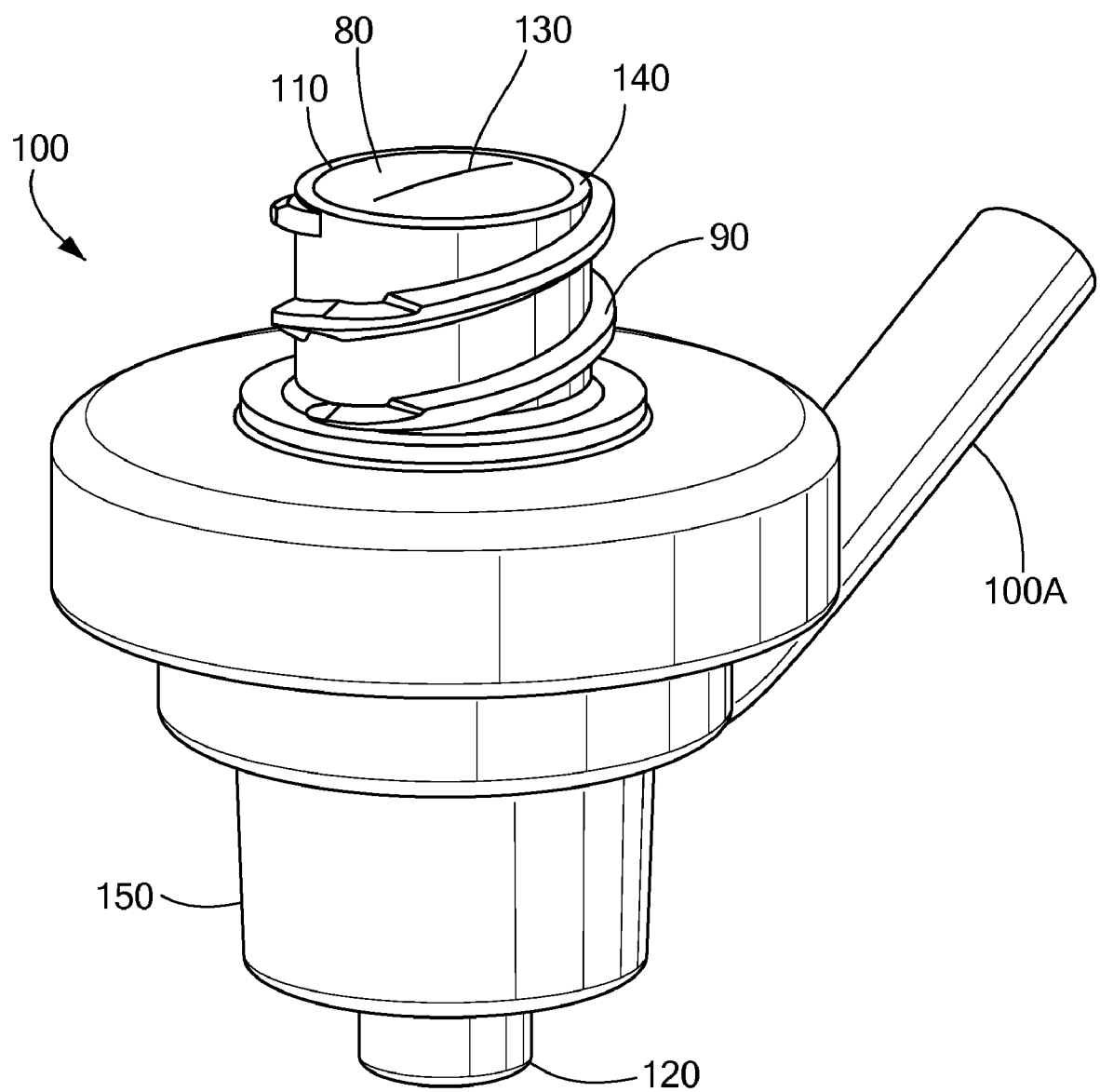
FIG. 2B schematically shows a perspective view of a medical valve of FIG. 2A with a Y-site branch.

FIG. 2A schematically shows a perspective view of the medical valve 10 shown in FIG. 1, while FIG. 2B schematically shows the same valve with a Y-site branch (discussed below). In illustrative embodiments and primarily with reference to FIG. 2A, the valve 10 is configured to have a substantially positive fluid displacement (e.g., about five to fifty microliters, or about five to fifteen microliters) during insertion of the instrument 40 into the valve 10, and a substantially neutral fluid displacement (between about plus or minus 1 microliter of fluid displacement, discussed below) during removal of the instrument 40 from the valve. In other words, insertion of a syringe 40 causes a positive fluid displacement at the distal end of the valve 10 (distal port 120, shown in FIG. 2A and discussed below), while syringe removal causes essentially no or negligible fluid displacement at the distal end of the valve 10.

In this context, fluid displacement generally refers to the flow of fluid through the distal port 120 of the valve 10 (discussed below). Accordingly, a positive fluid displacement generally refers to fluid flowing in a distal direction through the distal port 120, while a negative fluid displacement generally refers to a fluid flowing in a proximal direction through the distal port 120. The positive/neutral nature of the valve 10 is discussed in greater detail below. Of course, not all embodiments exhibit this quality. For example, in alternative embodiments, the valve 10 may have a positive fluid displacement when the instrument 40 is inserted, and a negative fluid displacement when the instrument 40 is withdrawn. In fact, the valve 10 can exhibit other positive/negative/neutral fluid displacement qualities upon instrument insertion and withdrawal. For example, the valve 10 could exhibit a positive fluid displacement upon insertion, and a positive fluid displacement upon withdrawal. Accordingly, discussion of positive/neutral is not intended to limit all embodiments of the invention.

It should be noted that the fluid displacements discussed herein refer to the "net" fluid displaced through the distal port 120. Specifically, during insertion or withdrawal of the instrument 40, the actual flow of fluid through the distal port 120 may change direction and thus, fluctuate. However, when considering this fluctuation, the net change in fluid flow through the distal port 120 should be 1) positive when the valve exhibits a "positive fluid displacement," and 2) negative when the valve exhibits a "negative fluid displacement." In a similar manner, a substantially neutral fluid displacement occurs when, as noted above, the valve 10 has a net fluid displacement of about plus or minus one microliter. Of course, the fluid displacement of the valve 10 is discussed herein in terms of one stroke of the instrument 40 (i.e., insertion or withdrawal of the instrument 40).

Ideally, a valve with a neutral displacement has 0.0 microliters of positive or negative fluid displacement. As suggested above, however, in practice, a neutral displacement actually can have a very slight positive or negative displacement (e.g., caused by a manufacturing tolerance), such as a displacement on the order of positive or negative one microliter, or less. In other words, in such embodiments, the volumes of fluid forced through the distal port 120 in a neutral displacement valve are negligible (ideally zero microliters) and should have a negligible impact on the goals of the valve.

Some embodiments may have a positive fluid displacement upon insertion, but a very low positive fluid displacement or very low negative fluid displacement upon withdrawal. For example, such valves 10 may have a negative fluid displacement of about one to two microliters (i.e., about one to two microliters of fluid drawback, which is proximally directed), or about one to two microliters positive fluid displacement (i.e., about one to two microliters of positively pushed fluid, which is distally directed). Although such amounts are in the positive or negative fluid displacement ranges, they still should represent a significant improvement over valves that exhibit higher positive or negative fluid displacements upon withdrawal.

The neutral, positive, or negative fluid displacement of a valve may be corrupted by manual handling of the valve 10, catheter 70 or the instrument 40 during the fluid transfer. For example, a slight inward force applied to the shaft of the syringe 40 (e.g., by the nurse's hand when simply holding the syringe 40) can have the effect of adding a positive fluid displacement from the syringe (when the force is applied) and, ultimately, through the valve 10. In fact, releasing this force from the syringe 40 actually may draw fluid proximally, causing a negative fluid displacement that further corrupts fluid displacement. These effects, however, should not be considered when determining the nature of fluid displacement through the distal port 120. To overcome the problem noted above with regard to squeezing the syringe shaft, for example, the nurse 20 can hold another part of the syringe that does not contain the fluid (e.g., stubs at the proximal end of the syringe 40).

To accomplish these desired goals, the valve 10 has a housing 100 forming an interior having a proximal port 110 for receiving the instrument 40, and the noted distal port 120 having the discussed fluid displacement properties. The valve 10 has an open mode that permits fluid flow through the valve 10, and a closed mode that prevents fluid flow through the valve 10. To that end, the interior contains a valve mechanism that selectively controls (i.e., allow/permits) fluid flow through the valve 10. The fluid passes through a complete fluid path that extends between the proximal port 110 and the distal port 120.

It should be noted that although much of the discussion herein refers to the proximal port 110 as an inlet, and the distal port 120 as an outlet, the proximal and distal ports 110 and 120 also may be respectively used as outlet and inlet ports. Discussion of these ports in either configuration therefore is for illustrative purposes only.

The valve 10 is considered to provide a low pressure seal at its proximal end 110. To that end, the proximal end 110 of the medical valve 10 has a resilient proximal gland 80 with a resealable aperture 130 that extends entirely through its profile. The aperture 130 may, for example, be a pierced hole or a slit. Alternatively, the proximal gland 80 may be molded with the aperture 130. When the valve 10 is in the closed mode, as shown in FIG. 2A, the aperture 130 may be held closed by the inner surface of the housing 100. In that case, the inner diameter of the housing 100 at the proximal port 110 is smaller than the outer diameter of the proximal gland 80 and thus, the housing 100 squeezes the aperture 130 closed. Alternatively, the gland may be formed so that the aperture 130 normally stays closed in the absence of radially inward force provided by the inner diameter of the proximal port 110. In other words, the proximal gland 80 is formed so that the aperture 130 normally is closed.

Figure 3:
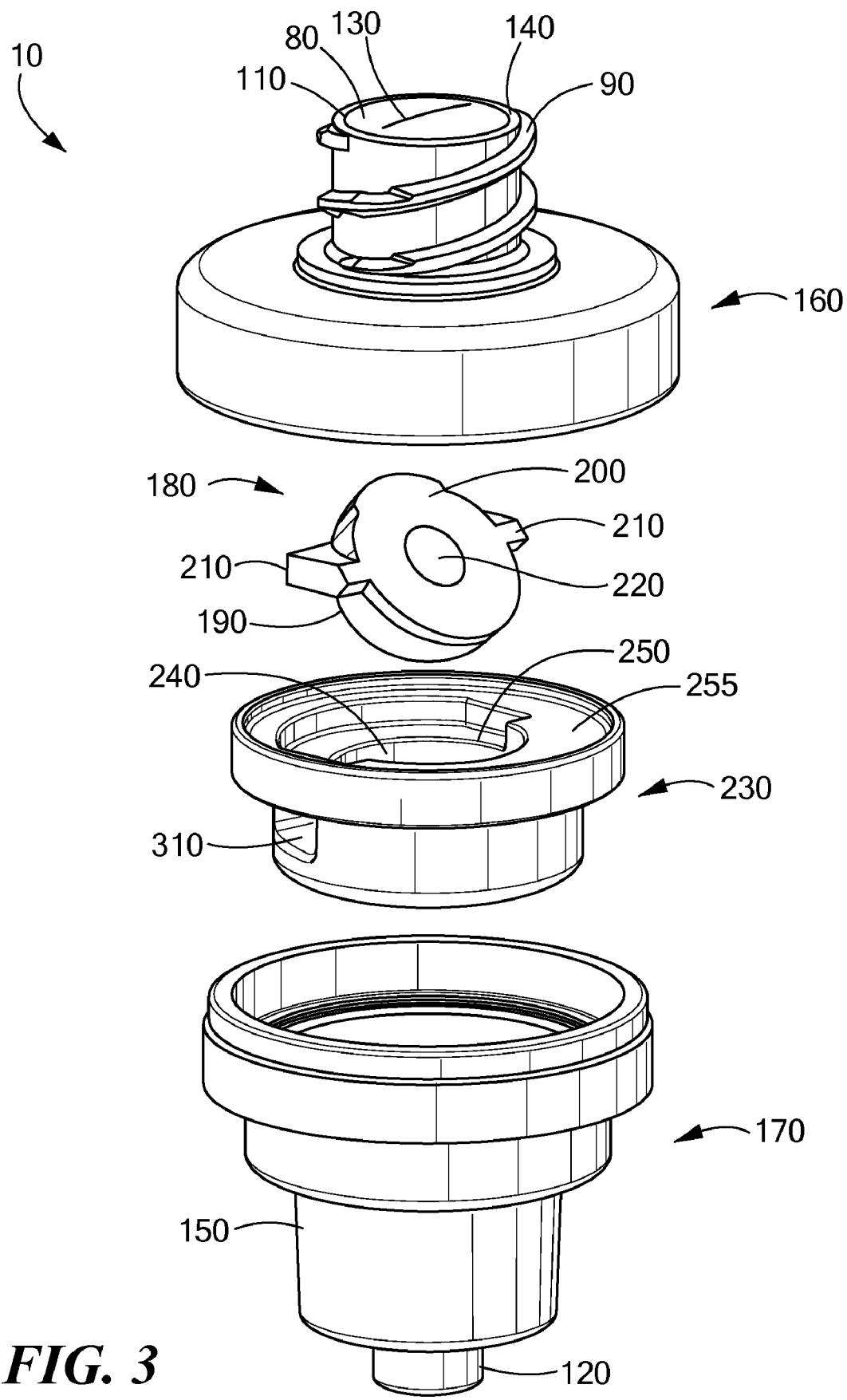
FIG. 3 schematically shows a perspective exploded view of the medical valve shown in FIG. 2A.

As suggested above, the proximal gland 80 is flush with or extends slightly above the exterior inlet face 140 of the inlet housing 160 (FIG. 3, discussed below). The proximal gland 80 and the exterior inlet face 140 thus present a swabbable surface, i.e., it may be easily wiped clean with an alcohol swab, for example, or other swab. Such valves typically have been referred to in the art as "swabbable valves." Various other embodiments, however, may relate to other types of valves and thus, not all embodiments are limited to swabbable valves. In addition, some embodiments may be used with instruments 40 having blunt tips that do not comply with the ANSI/ISO luer standard.

The outside surface of the valve proximal end 110 may also have inlet threads 90 for connecting the medical instrument 40. Alternatively or in addition, the proximal end may have a slip design for accepting instruments 40 that do not have a threaded interconnect. In a similar manner, the distal end of the valve 10 has a skirt 150 containing threads 280 (see FIG. 4A to 4G) for connecting a threaded port of the catheter of FIG. 1, or a different medical instrument, to the valve distal port 120. The proximal end inlet threads 90 and the distal end threads 280 preferably comply with ANSI/ISO standards (e.g., they are able to receive/connect to medical instruments complying with ANSI/ISO standards). In addition to the threads described above, the internal geometry of the inlet housing 160 (e.g., shown in FIG. 4A, discussed below) may taper in an opposite direction to that of a standard luer taper.

FIG. 3 schematically shows an exploded perspective view of the medical valve 10 shown in FIG. 1. As shown, the housing 100 includes an inlet housing 160 and an outlet housing 170 that connect to form the interior, which, as noted above, contains a valve mechanism. The inlet housing 160 and the outlet housing 170 may be joined together in a variety of ways, including a snap-fit connection, ultrasonic welding, plastic welding, or other method conventionally used in the art.

Generally, unlike the low pressure seal formed by the proximal gland 80, the internal valve mechanism should be capable of withstanding relatively high pressures. Accordingly, this internal valve mechanism is referred to as a "high pressure seal." To that end, the internal valve mechanism includes a moveable member 180 that cooperates with a resilient member 230 (without limiting scope, hereinafter referred to as "internal gland 230" for convenience) to selectively open and close the fluid channel through the housing 100. In the embodiment shown in FIG. 3, the moveable member is a rotating member 180 formed from a relatively rigid material (e.g., medical grade plastic), while the internal gland 230 is a resilient gland member (e.g., medical grade silicone). To provide their valving function, the internal gland 230 has a concavity that supports the rotating member 180 within the interior of the valve housing 100. Details of their interaction is discussed below.

Accordingly, as noted above, the valve 10 may be considered to have dual seals—a low pressure seal at the proximal end, and a high pressure seal within the interior. As an example, when used in the manner shown in FIG. 1, the low pressure seal may be able to withstand pressures of up to (on the order of) about nine PSI and greater. The high pressure seal, however, may be able to withstand pressures up to (on the order of) about 45 PSI and greater. Of course, the materials and geometry of the internal components can be adjusted to change these values. Those skilled in the art therefore should design the valve 10 to operate effectively when subjected to pressures generally produced during anticipated uses.

In alternative embodiments, the rotating member 180 is formed from a relatively resilient material, while a relatively rigid member is substituted for the internal gland 230. It also should be noted, however, that some embodiments use other types of movable members that are not primarily rotationally movable. For example, in those embodiments, the movable member may slide linearly. Accordingly, in such embodiments, a moveable member that is capable of selectively permitting fluid flow in the defined manner should be considered to be within the scope of this invention.

Although not clearly shown in FIG. 3 (but more clearly shown in later figures), the rotating member 180 has a substantially hemispherical surface 190 supported by the internal gland 230, and a generally proximally exposed surface 200 for contacting the instrument 40 when inserted through the inlet port 110. As discussed below, this contact between the instrument 40 and proximally exposed surface 200 effectively actuates the rotational member 180, thus opening the valve 10. This proximally exposed surface 200 may be flat, or have some contour (e.g., waves, grooves, and/or protrusions) or texture. Discussion of it as a flat surface therefore is for illustrative purposes only. In a similar manner, the hemispherical surface 190 may have another shape that enables rotation (e.g., an elliptical, cylindrical, or hyperbolic shape). Discussion of a hemispherical shape therefore is for illustrative purposes only.

In addition to the proximally exposed surface 200 and substantially hemispherical surface 190, the rotating member 180 also has a pair of a protruding members 210 that are not parallel to the proximally exposed surface 200. The protruding members 210 help support the rotating member 180 within the internal gland 230, and, as discussed in greater detail below, aid in biasing the rotating member 180 toward the closed position. To facilitate fluid flow through the fluid channel, the rotating member 180 also has a through channel 220 that, when in the open mode, channels fluid flow through the rotating member 180 and the valve 10.

The internal gland 230 has a recessed surface 240 for receiving and supporting the rotating member 180. When in the closed mode, the internal gland 230 covers the distal outlet 222 of the channel 220 through the rotating member 180. By covering the distal outlet 222 of the channel 220, the internal gland 230 may not necessarily seal at that point. In other words, fluid still may leak from the channel 220 and traverse along the recessed surface 240. As discussed below, the internal gland 230 has an additional sealing feature (e.g., a flange 294 in one embodiment, discussed below) to prevent such fluid leaking to or from the channel 220 from entering the portion of the fluid path in communication with the distal port 120.

In alternative embodiments, however, the internal gland 230 does seal the distal outlet 222 of member channel 220 when the valve 10 is in the closed position. To that end, the internal gland 230 may be molded to have a relatively tight fit at that point. Such a fit, however, may increase the resistance of opening and closing the valve 10.

Moreover, in preferred embodiments, the recessed surface 240 effectively is a concavity that generally conforms to the radius of the hemispherical surface 190 of the rotating member 180. In other words, the radius of the hemispherical surface 190 is about the same as the radius of the recessed surface 240 to effectively form a close, registration fit. Other embodiments, however, do not have this relationship. In those cases, the concavity 240 can have a different radius that that of the hemispherical surface 190 (e.g., smaller or larger), or may be a different shape (e.g., elliptical, oval, etc. . . . ). Operation of and various features of the rotating member 180 and the internal gland 230 are discussed in greater detail below.

Figure 4A:
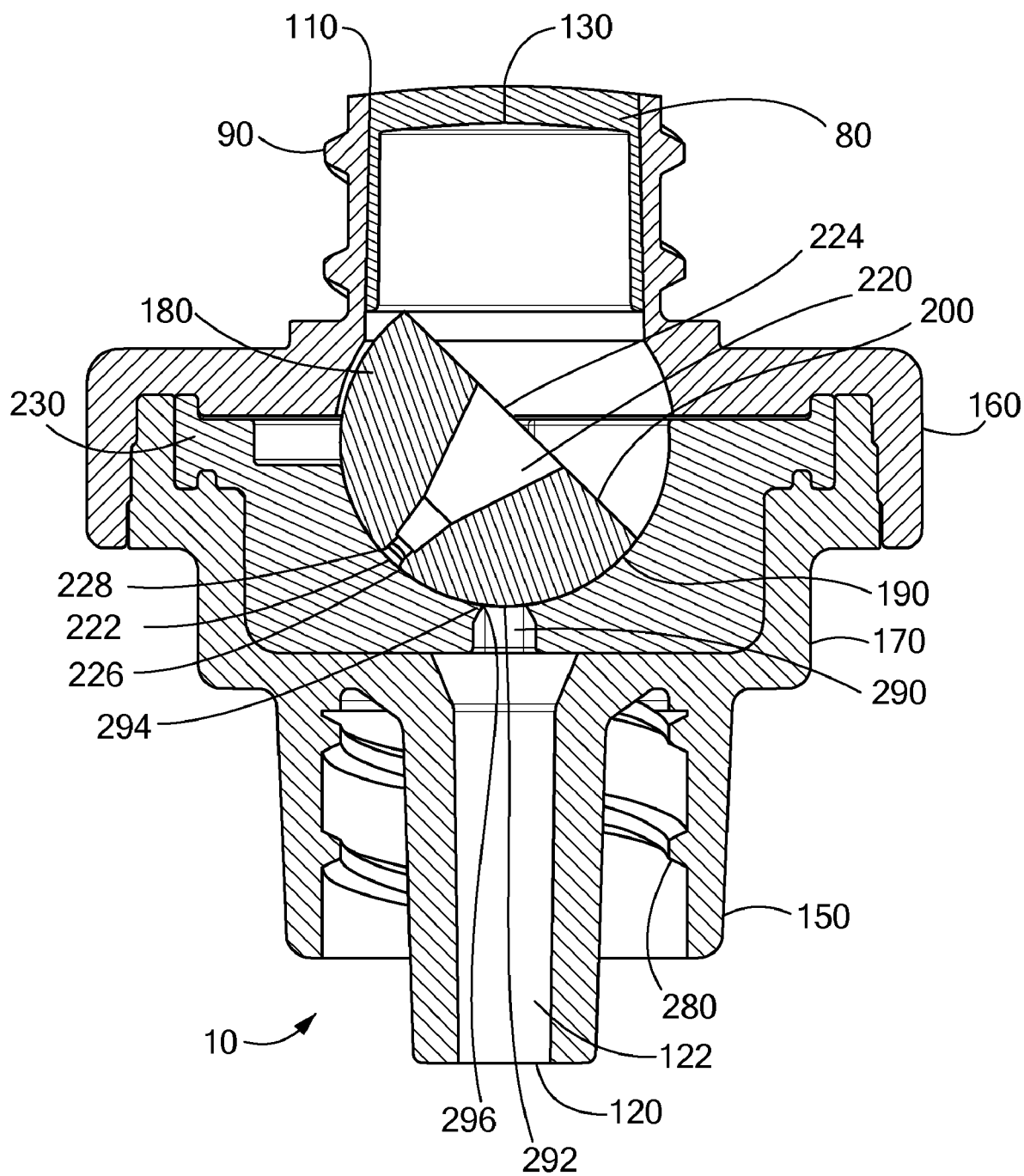
FIGS. 4A-4G schematically show cross-sectional views of the valve shown in FIG. 2A along line 4-4. These figures show the general progression of the valve as it transitions between open and closed modes.

As discussed above, FIG. 3 shows five pieces that form the valve 10 (i.e., the proximal gland 80, the inlet housing 160, the rotating member 180, the resilient member/internal gland 230, and the outlet housing 170). Different manufacturing processes form each part, which subsequently are assembled to form the valve 10. As shown in FIG. 4A (discussed in detail below), the internal gland 230 is compressed between the inlet housing 160 and outlet housing 170. This compression effectively forms a seal that mitigates the likelihood that fluid can leak in the interface between the housing portions 160/170 and the internal gland 230. In other words, the internal gland 230 forms a seal between it and the housing portions 160/170.

Alternative manufacturing techniques, however, can reduce the total number of components, and therefore simplify assembly. In particular, the proximal gland 80 and the inlet housing 160 can be manufactured in a "two-shot" or "over-mold" process. As known by those in the art, the two-shot manufacturing process creates one piece formed with two materials (i.e., the elastomeric proximal gland 80 material and the material forming the rigid inlet housing 160) that are chemically bonded to one another. In a similar manner, the internal gland 230 and the outlet housing 170 can be manufactured in a two-shot process to form a one-piece bottom housing. Therefore, the "two-shot" manufacturing process can reduce the total number of valve components to as few as three, significantly reducing assembly complexity. In addition, use of a two-shot process can significantly minimize the possibility of fluid leaking between the proximal gland 80 and inlet housing 160. In a similar manner, use of a two shot process can significantly minimize the possibility of fluid leaking between the internal gland 230 and the outlet housing 170.

FIGS. 4A through 4G schematically show cross-sectional views of the valve 10 of FIG. 2A across line 4-4. These figures schematically detail the general operation of the medical valve 10 as it transitions from the closed mode toward the open mode. Specifically, FIG. 4A shows the valve 10 in the closed mode when no syringe or other instrument 40 is inserted through the proximal opening 110. In this state, the internal gland 230 substantially covers the distal opening 222 of the rotating member channel 220.

This figure also details a number of additional features of the valve 10. In particular, it shows components that, when in the open mode, ultimately make up the flow path through the housing 100. The flow path begins at the inlet port 110 and into the interior chamber, through the member channel 220, and extends through a member flowpath 290, which is formed through the internal gland 230. As discussed in greater detail below, the proximal opening 292 of the member flowpath 290 has a flange 294 that effectively seals about the periphery of the flowpath 290. The ultimate flowpath extends through an outlet channel 122 that terminates at the distal port 120.

FIG. 4A also shows the internal gland 230 biasing the rotating member 180 to a closed position. Specifically, the resiliency of the internal gland 230 acts as a spring that, from the perspective of the configuration in FIG. 4A, provides a generally continuous biasing force in a clockwise direction. As discussed below, a sufficient force applied by the instrument 40 against the rotating member 180 overcomes this bias to ultimately open the valve 10.

Figure 4B:
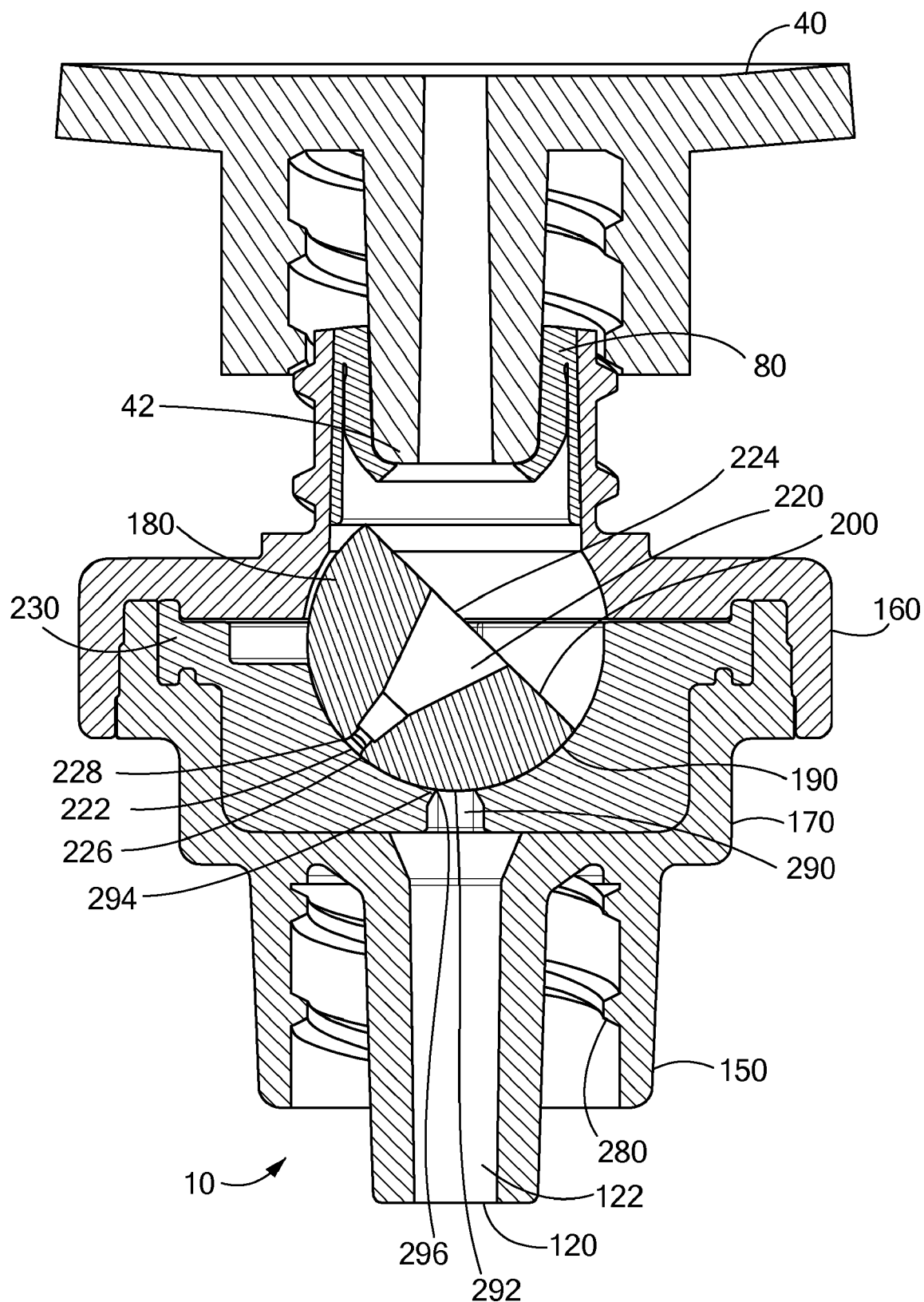
Figure 4C:
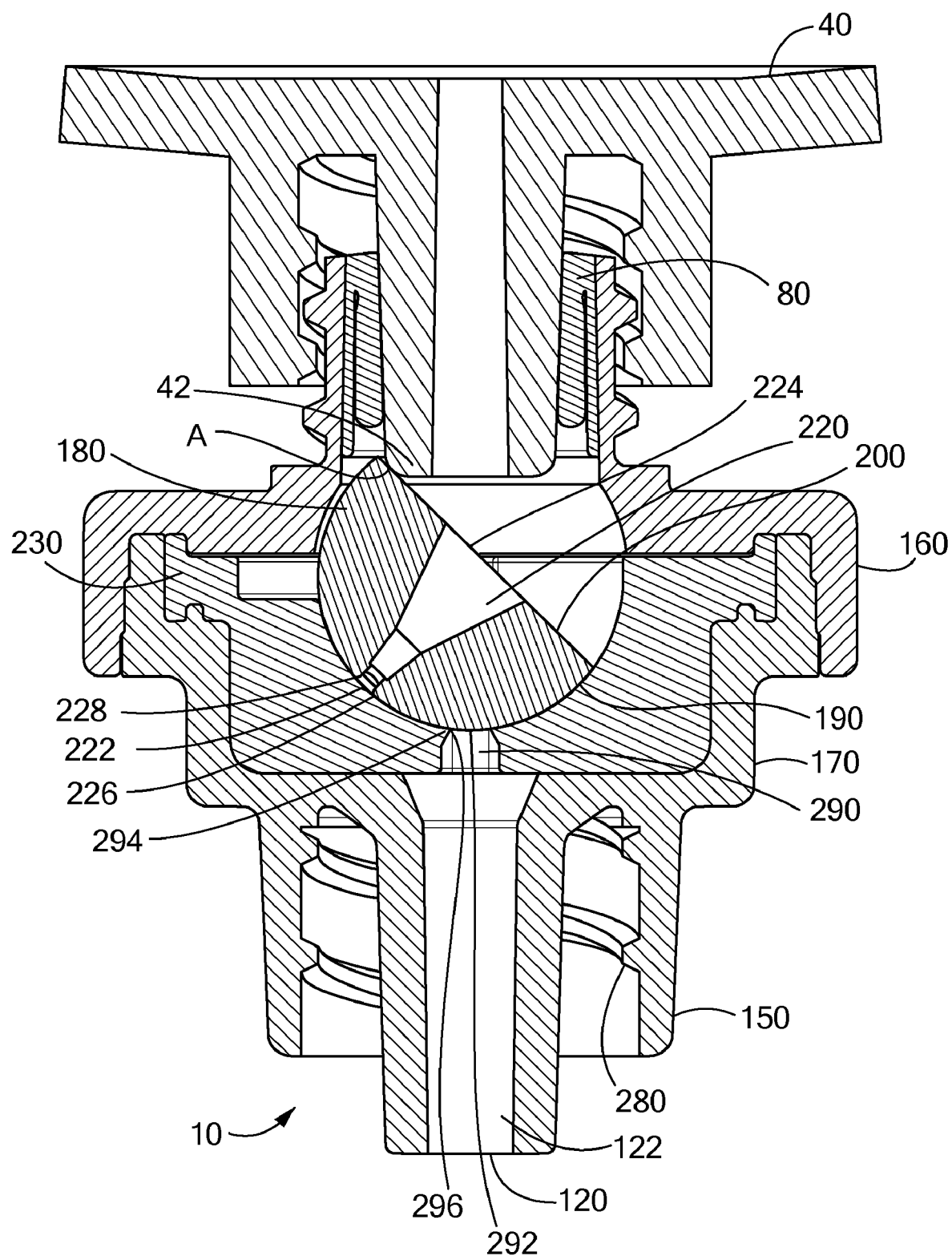

Insertion of a medical instrument 40 into the proximal port 110 opens aperture 130 in the proximal gland 80 (FIG. 4B). The aperture 130 effectively forms a seal about the outer diameter of the luer tip 42 of the instrument 40 to prevent fluid flow proximal of the proximal gland 80. The instrument 40 continues distally moving until it contacts the surface 200 of the rotating member 180, which is proximally exposed, at least at the initial point of contact, shown in FIG. 4C as surface A. As shown, the instrument 40 takes up a significant portion of the available volume within the interior of the housing 100. Accordingly, this produces a distally directed pressure against any priming fluid (e.g., saline) within the interior. During a corresponding withdrawal stage, this volume taken up by the instrument 40 effectively leaves a relatively small amount of fluid within the primed valve 10.

During insertion, the proximally exposed surface 200 of the rotating member 180 acts as a camming surface against the medical instrument 40. Distally directed force applied to the proximally exposed surface 200 at surface A by the medical instrument 40 begins to rotate the rotating member 180 toward the open position/mode. Specifically, the rotating member 180 rotates about an axis that is generally orthogonally aligned with the longitudinal axis of the valve 10. This force at surface A effectively forms a lever arm extending between surface A and the point of rotation. When the force applied by this effective lever arm overcomes the bias force applied by the interior gland 230, the rotating member 180 begins rotating counter-clockwise toward the open mode.

In general, the rotating member 180 does not move longitudinally. However, some incidental longitudinal movement may occur as the result of slight compression of the valve materials.

Figure 4D:
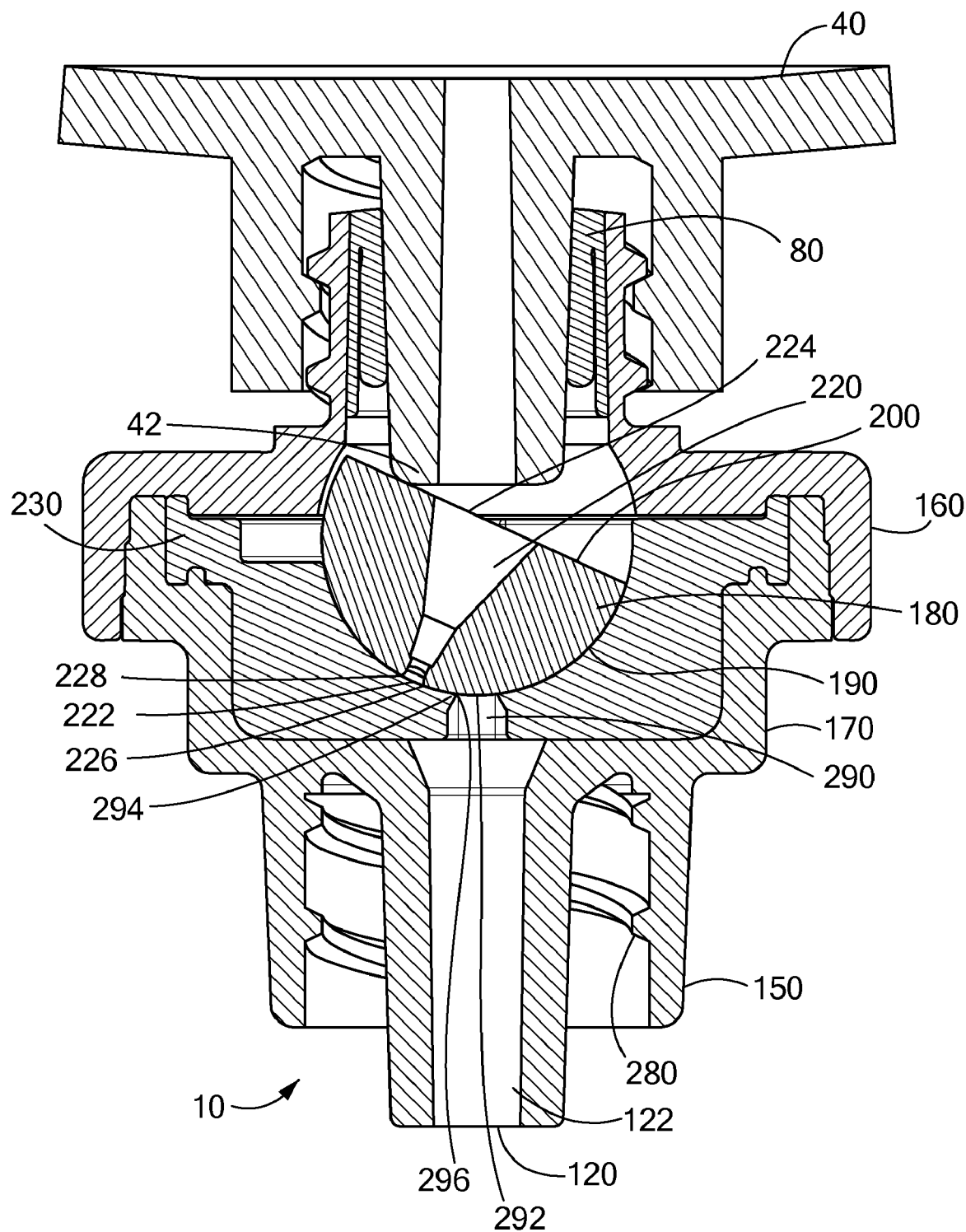

FIG. 4D shows the rotating member 180 rotated to an intermediate point in its opening stroke. To move from the position in FIG. 4C to the position of FIG. 4D, the instrument 40 slides along the proximally exposed surface 200, which, as noted above, acts as a camming surface. The noted effective lever arm gradually decreases, thus increasing opening resistance. In addition, the biasing force of the internal gland 230 also provides increased opening resistance as the rotating member 180 rotates. The threads 90 on the inlet port 110 mate with corresponding threads on the instrument 40, thus providing an assist in providing sufficient force to rotate the rotating member 180.

Also while moving between modes, the generally hemispherically shaped surface 190 of the rotating member 180 slides along the corresponding portion of the internal gland 230. While sliding, as noted above, the member channel 220 may not be fully sealed. Fluid leaking from the member channel 220, if any, should be blocked from passing through the flowpath 290 by the flange 294.

Figure 4E:
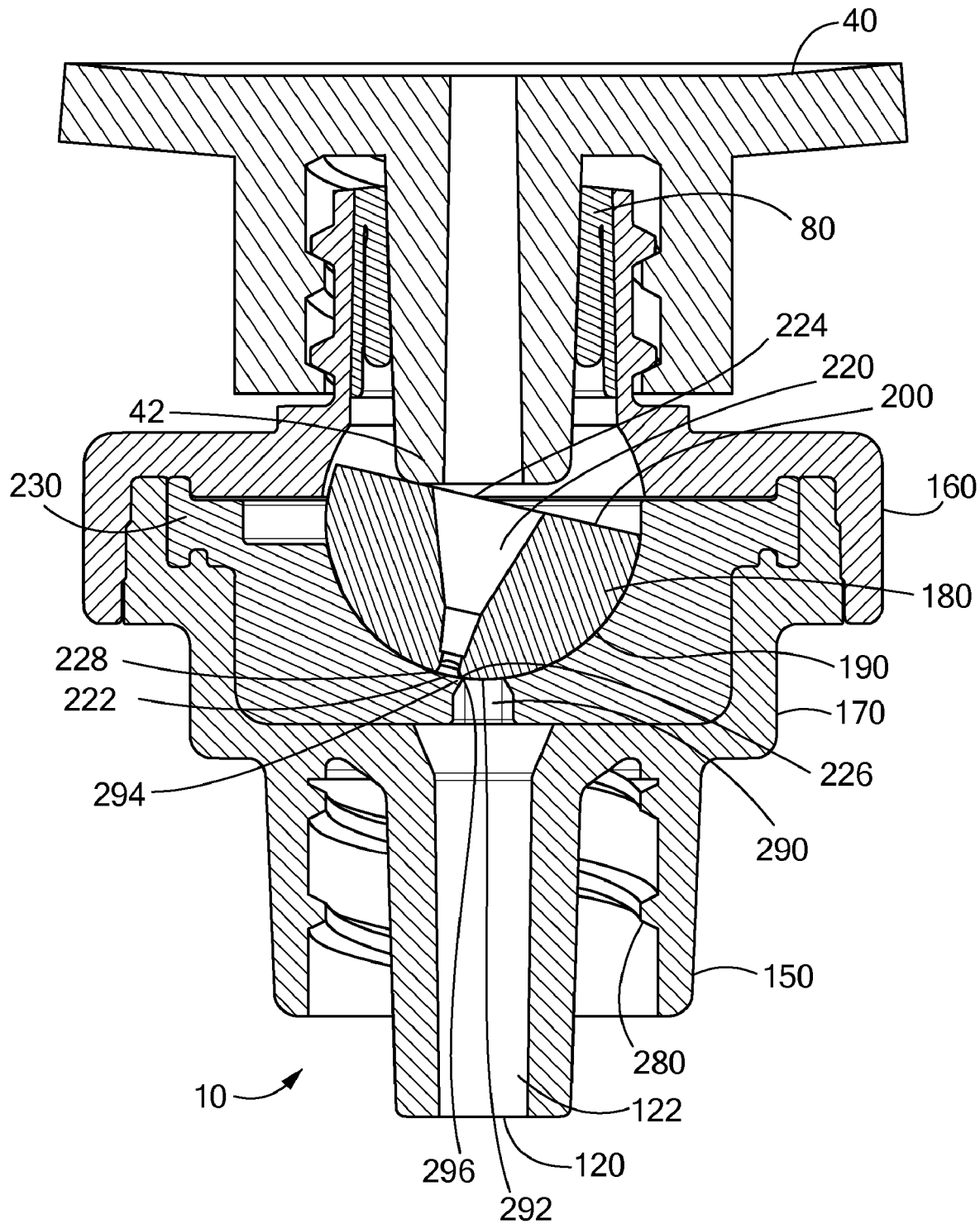
Figure 4F:
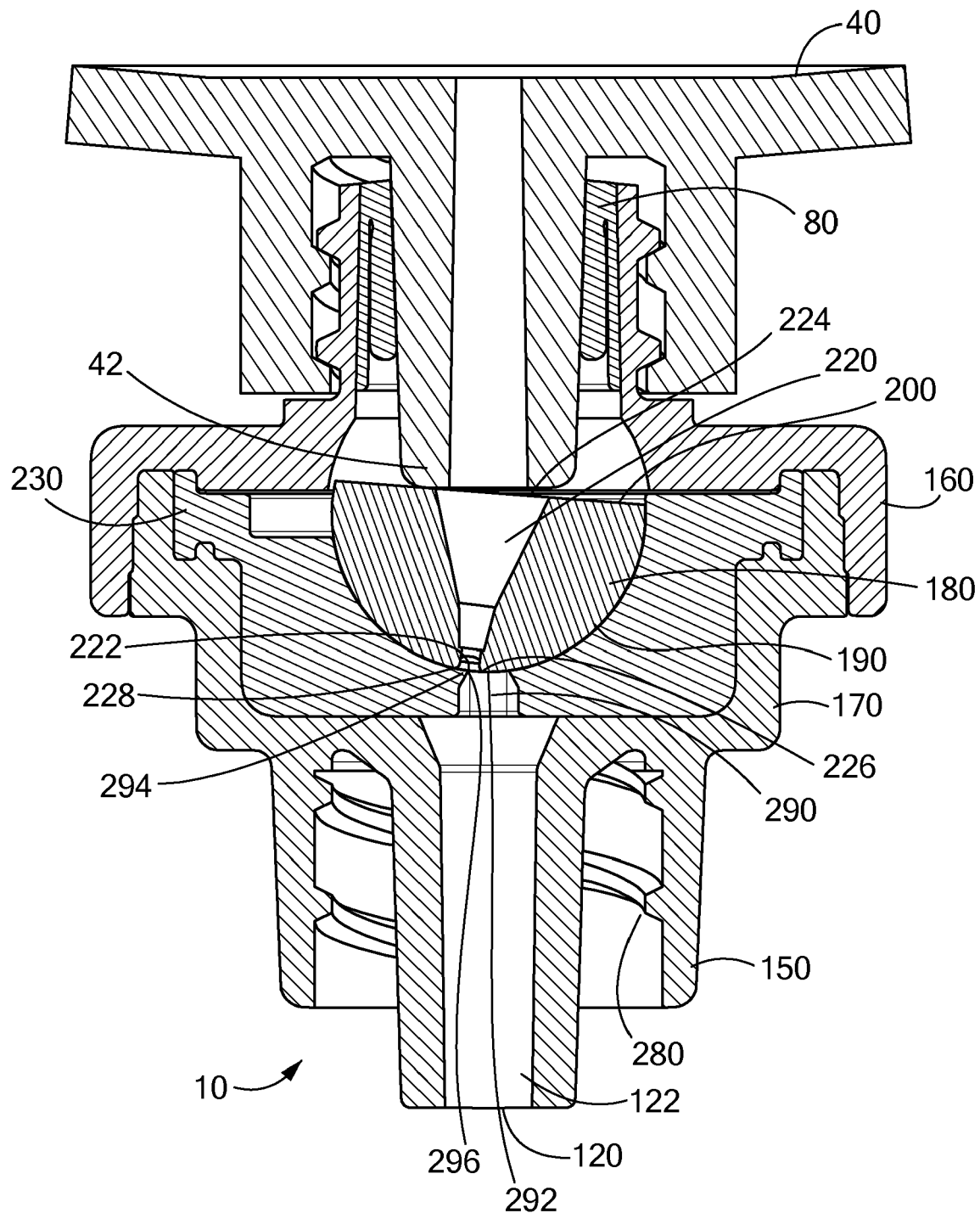

The rotating member 180 continues to rotate, sliding along the internal gland 230, until the leading edge 226 of the distal opening 222 of the member channel 220 almost passes the leading edge 296 of the flange 294 (FIG. 4E). Specifically, as shown in FIG. 4E, the rotating member 180 has rotated a significant amount although the valve 10 still is in a closed mode because the distal opening 222 of the member channel 220 remains fluidly disconnected from the proximal opening 292 of the member flow path 290. As the rotating member 180 rotates further (FIG. 4F), the valve 10 begins to open as the leading edge 226 of the distal opening 222 of the member channel 220 passes the first edge/lip 296 of the fluid path 290 through the internal gland 230. At this point, there is fluid communication between the valve proximal port 110 and distal port 120. Although some of the member channel 220 still is occluded at this point, the valve 10 may be considered to be in the open mode at this point.

Figure 4G:
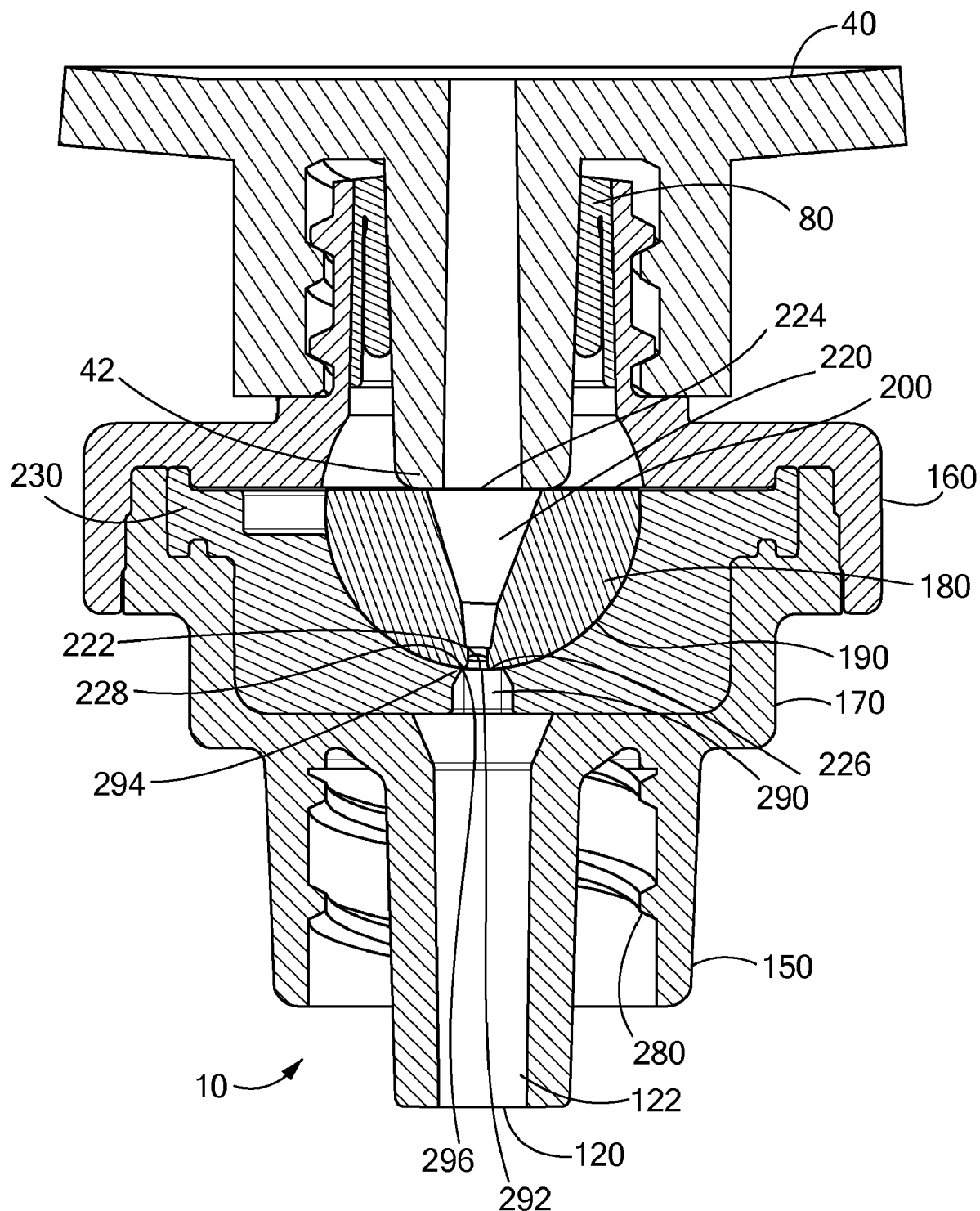

The rotating member 180 continues to rotate to the fully open position shown in FIG. 4G, in which the distal opening 222 is substantially completely exposed to the fluid path 290. Accordingly, in this position, the full flow path through the valve 10 is opened; namely, the member channel 220, fluid path 290, and the proximal port 110 and distal port 120 are in maximum fluid communication with one another, creating a fluid channel through the medical valve 10. As an example, the rotating member 180 of some embodiments rotates between about 15 and 60 degrees to traverse from the closed position of FIG. 4A to a fully open position as shown in FIG. 4G.

In accordance with illustrative embodiments, when the instrument 40 moves longitudinally at a constant rate, the rotating member 180 rotates at a changing rate (i.e., an increasing or decreasing rate, depending on the direction of movement of the instrument 40). In other words, the rotating member 180 rotates at a changing rate per longitudinal inch of movement of the instrument 40. Specifically, if the instrument 40 were inserted distally at a constant rate, the rotating member 180 would rotate at an increasing rate until the instrument 40 reaches its maximum insertion. In a corresponding manner, if the instrument 40 were withdrawn proximally at a constant rate, the rotating member 180 would rotate at an decreasing rate until the instrument 40 loses contact with the proximally facing surface 200.

In either case, the rotational speed of the rotating member 180 is at its maximum when in the fully open position. Accordingly, the distal opening 222 of the member channel 220 moves most rapidly as it rotates from the open mode (FIG. 4G) to the point of the closed mode shown in FIG. 4E. For any other arc of travel of similar length, the instrument 40 traverses distally a longer longitudinal distance. Of course, in practice, there is no requirement that the person controlling the instrument 40 insert or withdraw it at a constant rate. The rate of rotation thus is completely controlled by the rate of movement of the instrument 40, which, during use, can vary. Discussion of insertion and withdrawal at a constant rate is for illustration purposes only.

The rotating member 180 and internal gland 230 cooperate to cause this relationship between instrument insertion and rotating member rotation. Among other things, as noted above, as the medical instrument 40 moves longitudinally into the medical valve 10, the point at which the tip contacts the proximally exposed surface 200 changes. This change in point of contact changes the size of the above noted effective lever arm causing rotational movement. More specifically, as the point of contact moves closer to the center of the rotating member 180, the lever arm decreases, increasing the angular rate of rotation. In addition, the bias force of the interior gland 230 ensures that, at anticipated withdrawal speeds, the surface 200 maintains contact with the instrument 40 during withdrawal (except, of course, after the instrument 40 is withdrawn proximal of the position shown in FIG. 4C). Therefore, for this reason, the angular rate increases as the valve 10 transitions from the closed mode to the open mode and is at its maximum between FIGS. 4E and 4G.

This varying speed has a significant performance benefit. Specifically, the instrument 40 is drawn back a minimum distance to close the distal opening 222. Fluid drawback (i.e., negative fluid displacement), if any, through the distal port 120 therefore should be negligible because the instrument 40 moves a relatively short distance within the interior before the valve 10 closes. Accordingly, if properly configured, this should result in a substantially negligible fluid displacement (i.e., between about −1 and +1 microliters) through the distal port 120 of the valve 10.

Moreover, as shown in FIG. 4G, in a preferred embodiment, the rotating member channel distal opening 222 is located so that the trailing edge 228 of the rotating member distal opening 222 is located just past the first edge 296 of the member fluid path 290. This is in contrast to an alternative embodiment in which the distal opening 222 of the rotating member channel 220 is centered over the gland member fluid path 290. This positioning of the preferred embodiment provides an advantage in that a smaller amount of rotation is required to transition between the fully open to fully closed positions (e.g., from the positions of FIGS. 4G to 4E). In other words, compared to the noted alternative embodiment, when closing from a fully opened position, the instrument 40 does not move distally that additional distance that is required to rotate the distal opening 222 from a centered position to the position of FIG. 4G. Accordingly, the preferred embodiment discussed above should avoid negative fluid displacement caused by that additional movement.

Figure 5A:
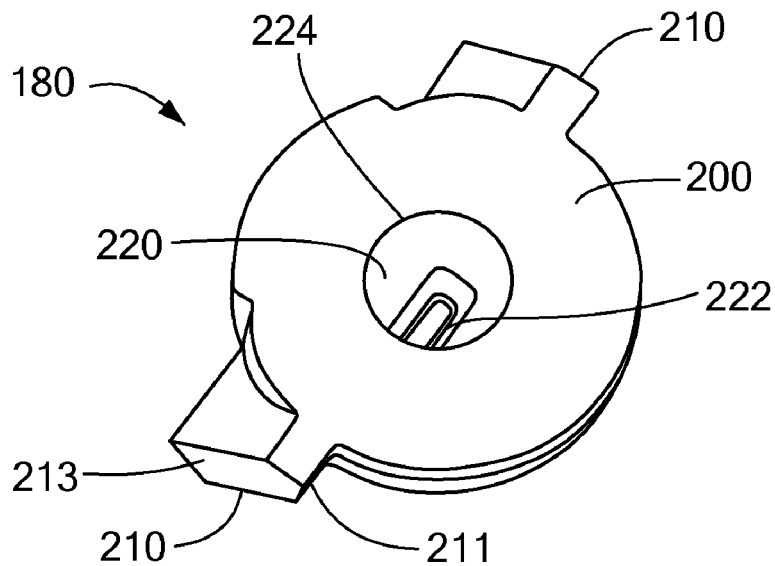
FIGS. 5A-5C schematically show perspective views of an illustrative embodiment of a rotating member within the valve of FIG. 2A.
Figure 5B:
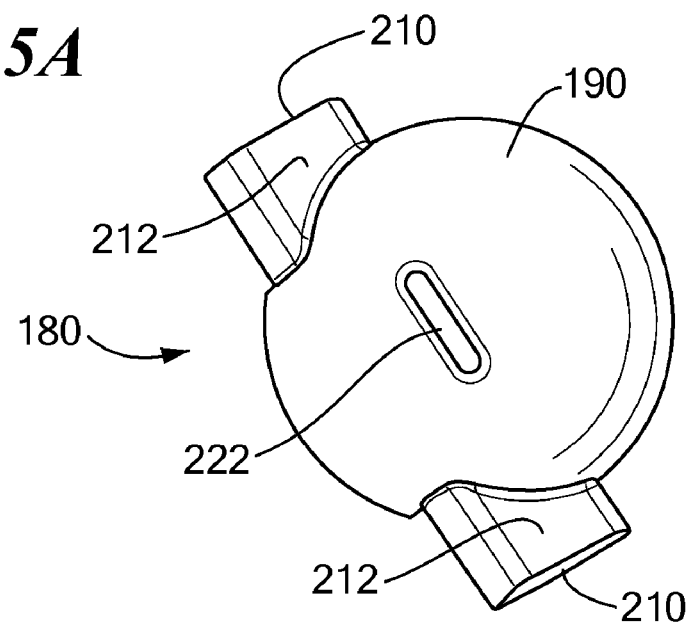
Figure 5C:
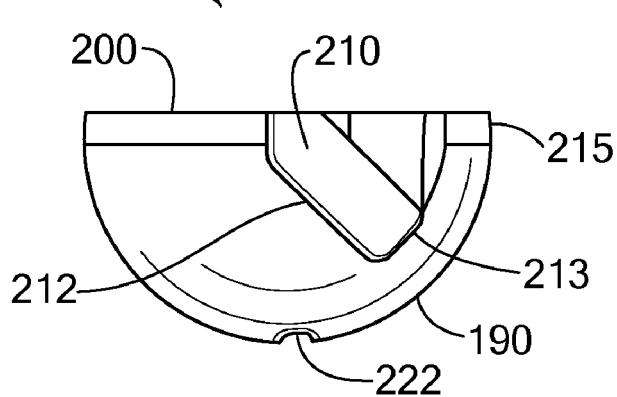

FIGS. 5A-5C and 6A-6F respectively schematically show additional views of the rotating member 180 and internal gland 230. Specifically, FIGS. 5A-5C schematically show more details of the rotating member 180 in the previous figures. As discussed above, the rotating member 180 may be generally hemispherical in shape and have protruding members 210 that interact with the internal gland 230 to bias the rotating member 180 toward the closed position. The protruding members 210 can be wing-like structures located on either side of the rotating member 180. Alternatively, the protruding members 210 may also be a single continuous structure that wraps around all or part of the rotating member 180. The protruding members 210 still may take on other arrangements. The discussed arrangements therefore are for illustrative purposes and not intended to limit the scope of all embodiments.

As shown in FIGS. 5A and 5C, the protruding members 210 are oriented so that they are not parallel to the proximally exposed surface 200. Instead, the protruding members 210 diverge from the surface 200. This orientation causes the proximally exposed surface 200 to be oriented at an angle, relative to a transverse axis of the longitudinal axis, when the valve 10 is in the closed mode (see FIG. 4A).

In some embodiments, the rotating member 180 may also include a generally straight-walled portion 215 near its top, as shown in FIG. 5C. This straight walled portion 215 essentially forms a small cylinder at the top of the hemispherical surface 190 of the rotating member 180. This portion provides another benefit—it enhances sealing. Specifically, as the rotating member 180 slides along the internal gland 230, the straight-walled portion 215 projects slightly into the internal gland 230. This effectively creates an additional seal between the rotating member 180 and the internal gland 230 to mitigate fluid leakage between the two members. In some embodiments, the length of this straight-walled portion 215 is approximately 0.020 inches.

The protruding members 210 also may be off-set from the center of the rotating member 180. For example, as shown in FIGS. 5A and 5C, the protruding members 210 (e.g., "wings 210") may start at the top of the rotating member 180 at the proximally exposed surface 200, and then protrude outwardly and downwardly at an angle so that the wing 210 ends at edge 213, which is a distance away from the top and center of the rotational valve 10. Such a wing design is one embodiment that ensures that 1) the rotating member 180 is biased toward the closed position, and 2) the proximally exposed surface 200 is angled as noted above and still facing the proximal end of the valve 10.

In various figures, the proximally exposed surface 200 is substantially uninterrupted (e.g., no channels or grooves). However, in alternative embodiments, the proximally exposed surface 200 may include grooves 810A and 810B (FIG. 8A) to improve flushing and for directing fluid toward the inlet 224 of the member channel 220. The channels may extend radially outward from the center of the proximally exposed surface 200.

As mentioned above and shown in FIGS. 5A and 5B, the rotating member 180 has a member channel 220 extending from the proximally exposed surface 200 to the hemispherical surface 190. In preferred embodiments, the inlet 224 of the member channel 220 has a larger area than the distal opening 222. In fact, inlet 224 preferably has an area that is larger than that of the opening of the blunt tip of the medical instrument 40 used to open the valve 10. For example, the inlet 224 may have a greater area than that of the distal opening of a standard luer. In alternative embodiments, the inlet 224 has an area that is greater than the area defined by the outer dimension of the blunt tip 42 of the instrument 40.

As the member channel 220 transitions from the inlet 224 toward the distal opening 222, the channel 220 has a generally distally decreasing inner dimension. In other words, as the channel 220 transitions from inlet 224 toward the distal opening 222, the cross-sectional area of substantially the majority of the channel 220 generally decreases. This decrease may be gradual (e.g., a taper), stepped, irregular, or some other configuration.

In some embodiments, the distal opening 222 of the channel 220 is a different size and/or shape than that of the inlet 224. In accordance with illustrative embodiments of the invention, the distal opening 222 of the member channel 220 is configured to maximize fluid flow while permitting a relatively quick valve shut-off capability. To that end, as shown in FIG. 5B, the distal opening 222 preferably has a relatively large first inner dimension generally orthogonal to the direction of motion. This large dimension should enable the valve 10 to provide reasonably high flow rates. Conversely, the distal opening 222 has a corresponding relatively small dimension that is generally parallel to the direction of motion ("parallel dimension"). This parallel dimension should be selected to ensure that the valve turns off relatively quickly. In other words, because of the small size of this dimension, the rotating member 180 rotates a relatively small distance to fully transition from the fully open mode to the closed mode (e.g., FIG. 4E).

To those ends, the distal opening 222 may take on a number of shapes. Among others, it may be elliptical and configured so that its major axis is generally orthogonal to the direction of the rotational movement, and its minor axis is generally parallel to the direction of the rotational movement. In this orientation, the major axis provides the noted high fluid flow rate through the channel 220, while the minor axis allows for quick opening and closing, as described below. Although, an elliptical distal opening 222 is described, other shapes may be used to provide the same results. For example, among other shapes, the distal opening 222 may be substantially rectangular, rectangular with rounded corners, or oval. In some embodiments, the major axis may be about two or more times the length of the minor axis.

As best shown in FIG. 4G, the distal opening 222 illustratively is smaller than the proximal opening of the fluid path 290. The proximal opening of the fluid path 290 can be defined by a first lip and a second lip. The distance between the lips is greater than the minor axis of the distal opening 222, which allows the lips to seal around the outside of the distal opening 222. The proximal opening of the fluid path 290 can be a number of shapes (e.g., circular). In such embodiments, the first and second lips may be portions of the circle (e.g., each lip is one half of the circular opening). Sealing in this manner provides an essentially fluid tight fluid path between the rotating member 180 and the internal gland 230 when in the open mode.

Moreover, as also shown in FIG. 4G, the center line of the distal opening 222 of various embodiments is not aligned with the center of the proximal opening 292 of the fluid path 290. Instead, in various embodiments, the member channel 220 is tapered so that the distal opening 222 effectively is positioned toward one side of the fluid path proximal opening 292. For example, the center line of the distal opening 222 may be to the left of the fluid path proximal opening center line. As noted above, this helps to ensure that the trailing edge 228 of the distal opening 222 remains substantially aligned with or just past the first edge 296 of the fluid path 290 in the internal gland 230, and that minimal rotation is required to close the valve 10.

The rotating member 180 mates with and is supported by the internal gland 230, which is schematically shown in FIGS. 6A-6F. As mentioned above, the internal gland 230 has a concavity 240 that at least partially supports the rotating member 180, and may be a variety of shapes and sizes. For example, the size and shape of the concavity 240 may conform to the size and shape of the rotating member 180. Alternatively, the concavity 240 may be smaller or larger than the rotating member 180 and may be a different shape, such as elliptical, cylindrical, parabolic, or oval.

Figure 6B:
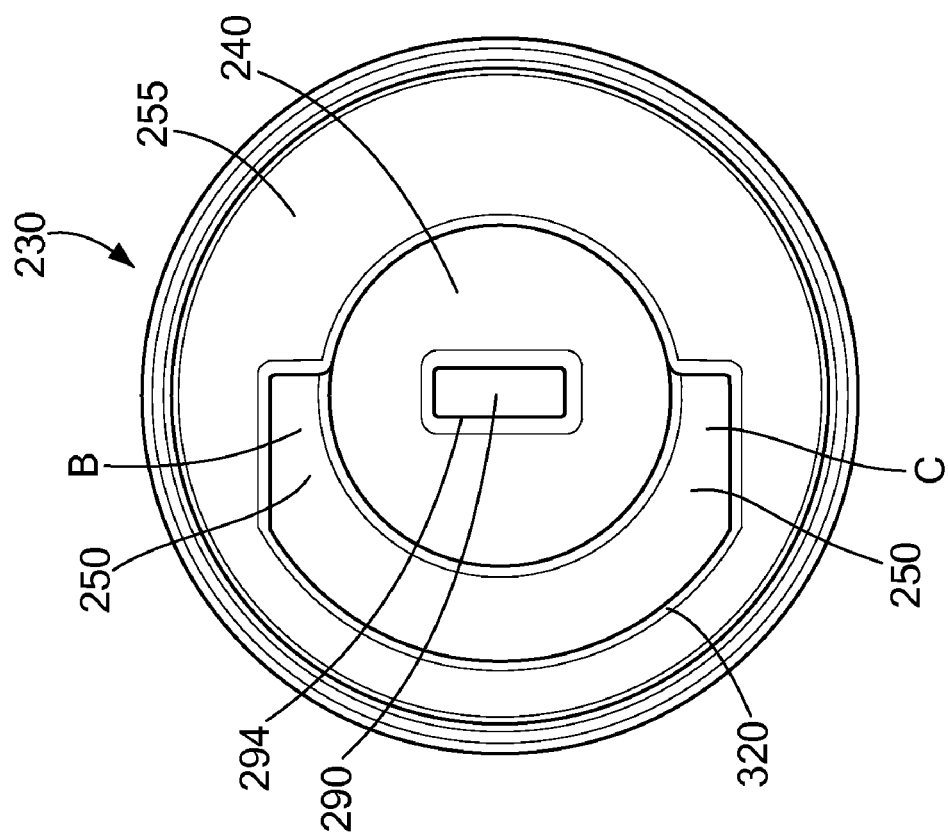
FIG. 6A to 6D schematically show perspective views of an illustrative embodiment of a resilient member within the valve of FIG. 2A.
Figure 6A:
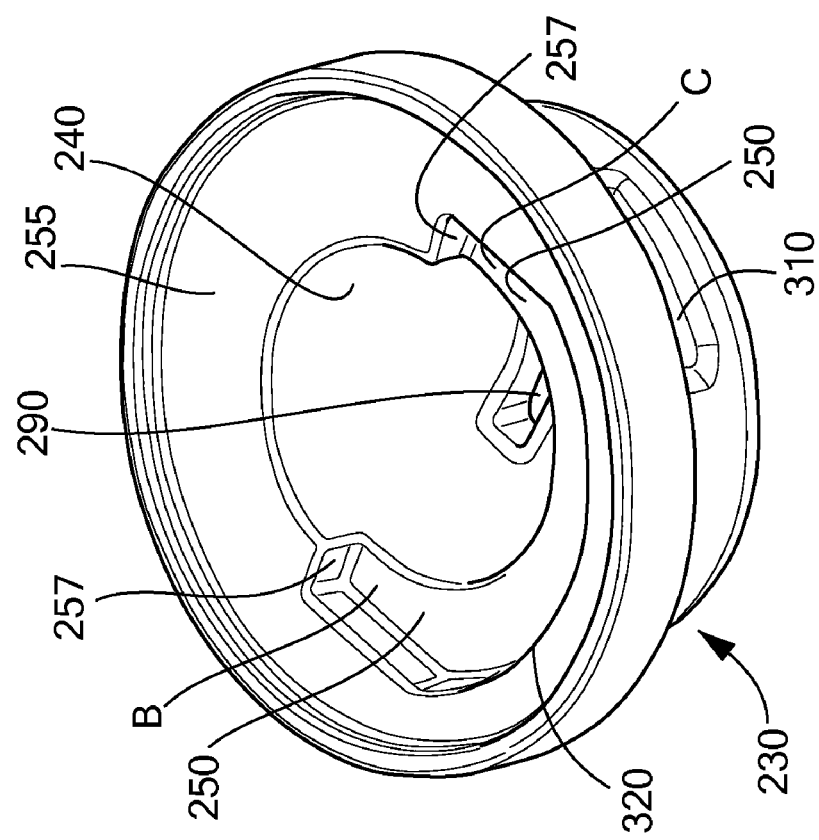
Figure 6C:
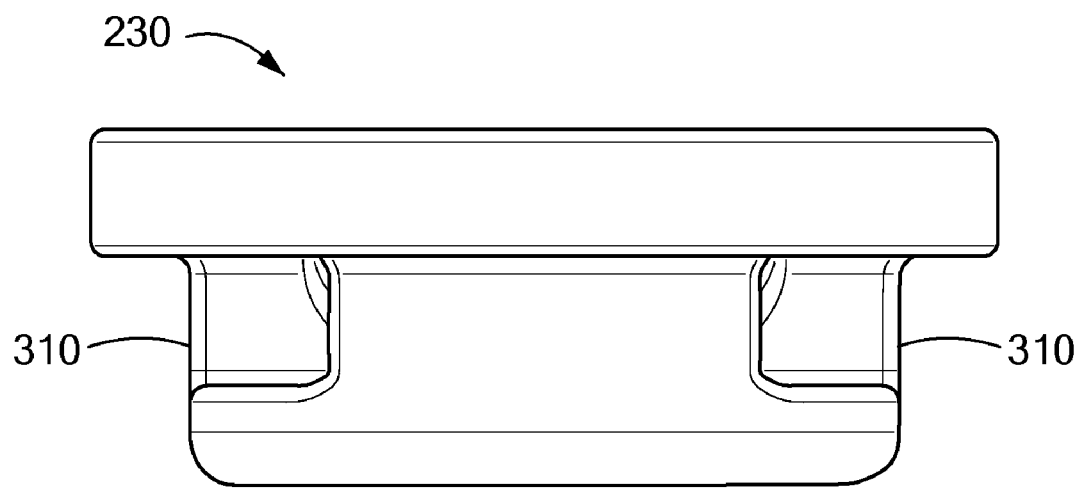
Figure 6D:
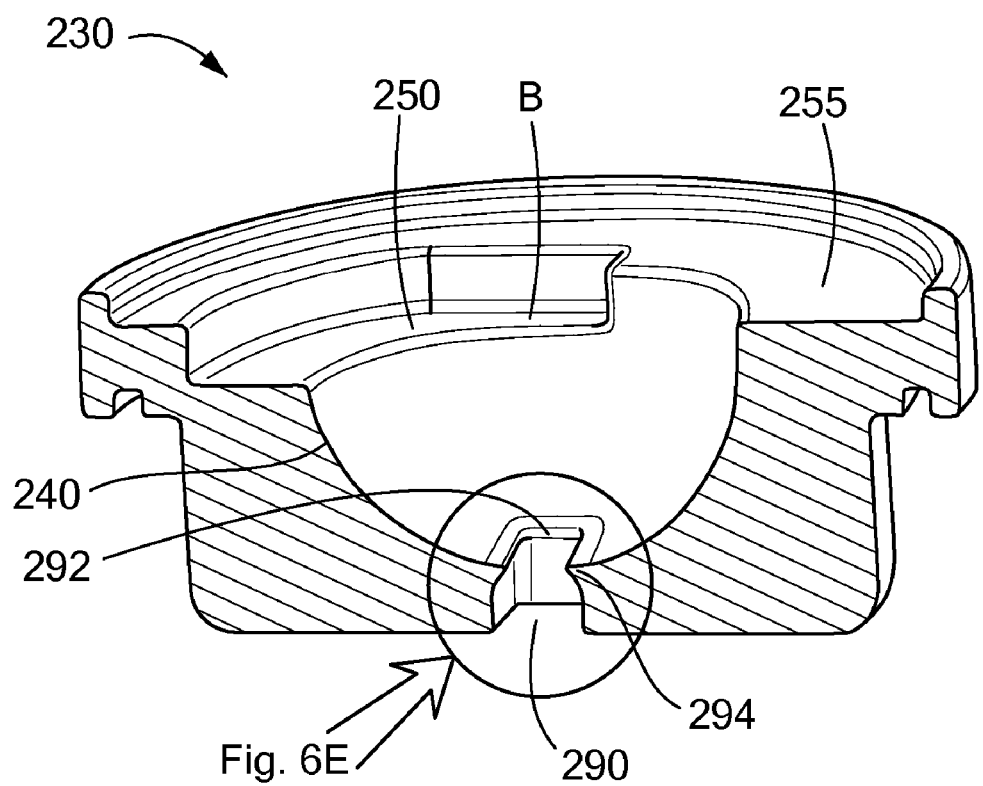
Figure 6E:
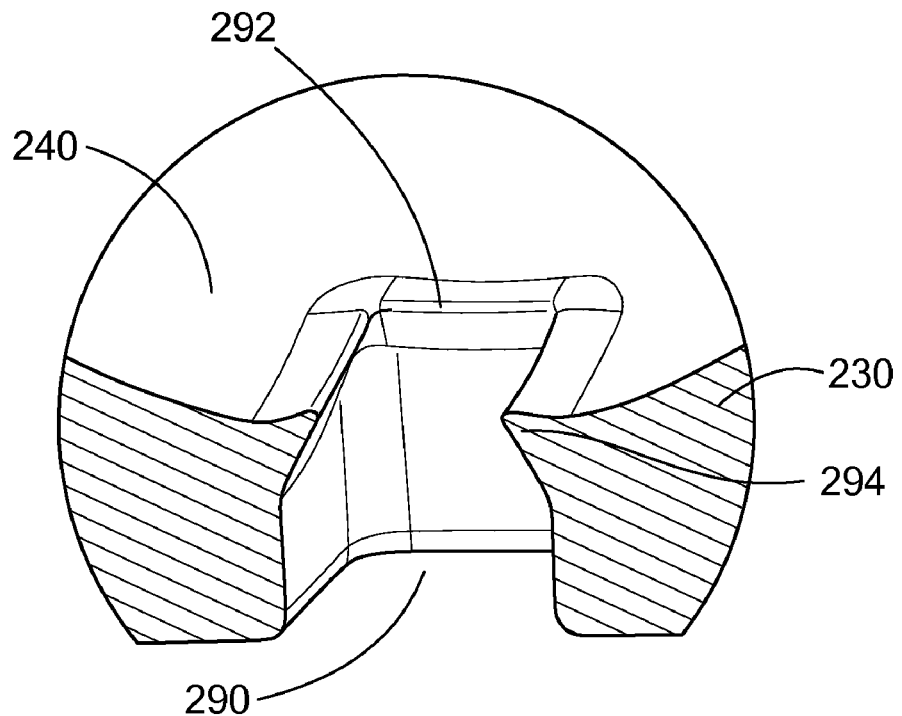
FIG. 6E schematically shows a close-up view of a portion of the resilient member shown in FIGS. 6A-6D. This close-up details a distal opening and a flange of the resilient member in a normal state (when not subjected to external forces, such as compression or stretching forces).
Figure 6F:
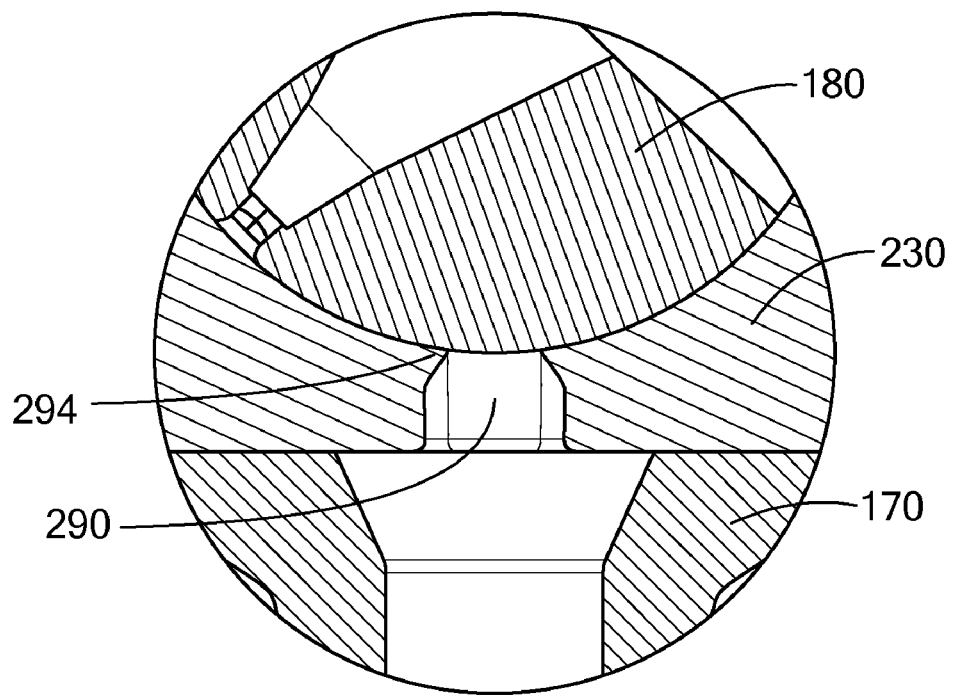
FIG. 6F schematically shows a close-up view of the distal opening and flange when not in the normal state—in this case, with the rotating member in place and thus, compressing the flange.

As noted above, the internal gland 230 normally has a flange 294 generally surrounding the proximal opening 292 of the gland fluid path 290. In this context, the term "normally" is used to connote the shape of a resilient member (e.g., the internal gland 230) when not subjected to external forces (e.g., when the internal gland 230 is separated from the valve 10). For example, FIG. 6E shows the flange 294 as extending outwardly and over the proximal end of the gland fluid path 290. This view thus shows the internal gland 230 when the rotating member 180 is not compressing the flange 294. In contrast, FIG. 6F shows the flange 294 when compressed by the rotating member 180. FIGS. 6E and 6F show the flange 294 as being integral to the resilient member 230 (e.g., formed as part of the resilient member 230). However, the flange 294 can be another type of structure that performs the described function and extends from the proximal end of the gland fluid path 290. For example, the flange 294 may be an o-ring located around the proximal end of the gland fluid path 290.

Specifically, the flange 294 normally not only protrudes upwardly into the concavity 240, it also protrudes out over the proximal opening 292 of the member flow path 290. As a result, both normally and when within the valve 10, the flange 294 narrows the proximal opening 292 as compared to the remainder of the flow path 290. As described in greater detail below, the flange 294 seals against the hemispherical surface 190 of the rotating member 180 as the valve 10 transitions between modes. Accordingly, when in the closed mode of FIG. 4A, the flange 294 prevents fluid leaking from the channel 220 from entering the flow path 290. In other words, when in the closed mode, the flange 294 maintains the fluid seal of the valve 10.

In a corresponding manner, when in the open mode of FIG. 4G, the flange 294 seals the perimeter of the distal opening 222 of the member channel 220. This ensures a substantially leak free connection between the member channel 220 and the flow path 290 in the open mode of FIG. 4G.

The internal gland 230 also has a mating surface 250 that mates with the wings 210 of the rotating member 180. The mating surface 250 may be recessed from the top surface 255 of the internal gland 230 to create vertical walls 257 between the top surface 255 and the mating surface 250. In a preferred embodiment, the wings 210 sit at surfaces B and C, which are considered "complimentary portions" of the internal gland 230 (i.e., complimentary to the wings 210). These surfaces B and C support the rotating member 180 within the internal gland 230 and cooperate to provide the bias to the rotating member 180. Specifically, the edges 211 of wings 210 preferably maintain contact with the vertical walls 257 at all times, even as the valve 10 transitions between open and closed. Alternatively, some embodiments have no such constant contact. Moreover, as known by those in the art, silicone is not compressible. Accordingly, the internal gland 230 has a pair of recesses 310 below surfaces B and C that allow gland material (e.g., above the recesses 310) to deform into their space as the valve 10 transitions from the open to the closed mode.

Assembly processes position the rotating member 180 in the concavity 240 of the internal gland 230 so that the hemispherical surface 190 of the rotating member 180 sits within the cavity 240 and the wings 210 sit at surfaces B and C above the gland member recesses 310. The wings 210 are oriented so that the bottom surface 212 of each wing 210 lies flat on the mating surface 250, thus causing the proximally exposed surface 200 of the rotating member 180 to be proximally exposed and positioned at the above noted angle (see FIGS. 4A-4G). When fully assembled, the inlet and outlet housing 160 and 170 squeeze the wings 210 to hold the rotating member 180 in place, effectively biasing the rotating member 230 as discussed above. This connection also substantially limits axial and linear movement of the rotating member 230.

In certain embodiments, the wings 210 may be thicker than the height of the vertical walls 257. In such embodiments, the inlet and outlet housings 160 and 170 slightly compress the wings 210 into gland material when the valve 10 is assembled. This creates a seal between the bottom surface 212 of the wings 210 and the mating surface 250, which prevents fluid leakage. This connection also holds the rotating member 180 in place to seal the distal opening 222 of the rotating member 180 in the closed mode, and the member channel 290 when in the closed mode.

As an example, the rotating member 180 and internal gland 230 may be designed so that the wings 210 extend a small distance (e.g., about 0.005 inches) above the mating surface 255 when the valve 10 is not fully assembled. When the inlet and outlet housings 160 and 170 are coupled, the rotating member 180 will compress slightly into the gland material in the cavity 240, causing the bottom surface 212 of the wings 210 to contact the mating surface 250. This also creates a seal between the hemispherical surface 190 of the rotating member 180 and the concavity 240.

In certain embodiments, the mating surface 250 and the vertical walls 257 may be in the form of a C-shaped grove 320 cut into the top surface 255 of the internal gland 230. FIGS. 6A and 6B show an exemplary C-shaped grove 320; however, the grove may be any shape capable of receiving the wings 210. The C-shaped groove 320 may improve valve flushing by providing a uniform plane, thus minimizing places (e.g., crevices or corners) in which debris and fluids can collect.

As noted above and shown in FIG. 6F, the rotating member 180 compresses the flange 294, creating a contour that generally conforms to the hemispherical surface 190 of the rotating member 180. During operation, the flange 294 maintains contact with the hemispherical surface 190 and essentially wipes across the surface. By doing so, the flange 294 effectively creates a wiper seal against the hemispherical surface 190 of the rotating member 180. As also shown in FIG. 6F, the gland member flow path 290 is narrowed at the proximal end 292. Therefore, the inner dimension of the gland member flow path 290 increases from the proximal end 292 to the distal end 294.

Referring back to FIGS. 4A-4G, to reiterate with additional detail, as a user inserts the medical instrument 40 into the valve 10 and the rotating member 180 begins to rotate, the wings 210 begin to depress the gland material at surfaces B and C into the recesses 310. The recesses 310 and the elastomeric properties of the gland material provide a spring force in a direction opposing the motion of the wings 210, and bias the valve 10 toward the closed mode. The vertical walls 257 between the top surface 255 and the mating surface 250 substantially prevent the rotating member 180 from sliding, and essentially allow only rotational movement. The vertical walls 257 also cooperate to prevent the rotating member 180 from twisting generally about the longitudinal axis of the valve (or generally about an axis that is generally parallel with the longitudinal axis of the valve). In other embodiments, the vertical walls 257 are not necessary to prevent such sliding.

The hemispherical surface 190 of the rotating member 180 will continue to slide along the surface of the cavity 240 until the valve 10 is fully open, and the member channel 220 fluidly communicates with the member fluid path 290.

When the valve 10 is in the open mode, the flange 294 surrounding the member fluid path 290 creates a seal around the member channel 220, preventing fluid leakage between the rotating member 180 and the internal gland 230, and back through the valve 10.

Figure 7:
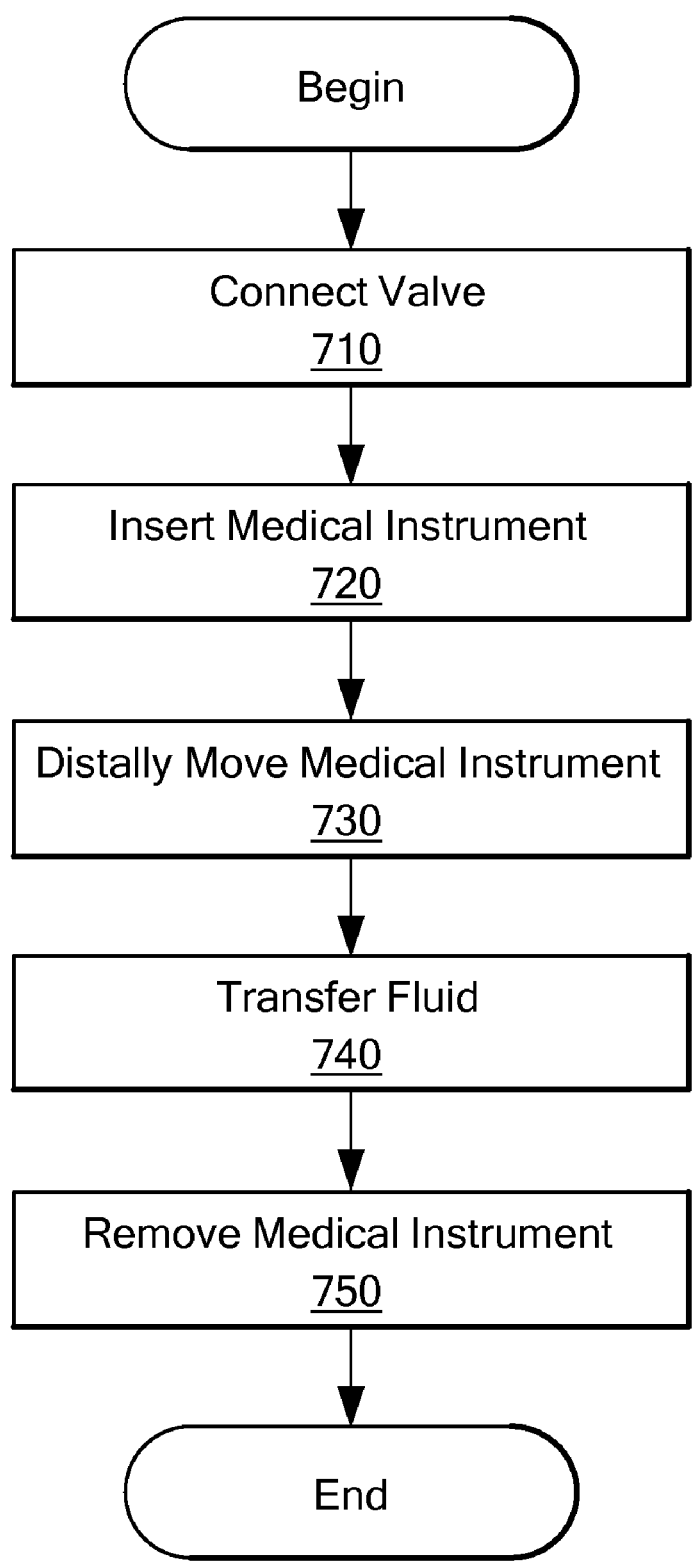
FIG. 7 shows a process of using the medical valve shown in FIG. 2A in accordance with illustrative embodiments of the invention.

FIG. 7 shows a process illustrating one of a plurality of illustrative uses of the medical valve 10. It is important to reiterate that, according to good medical practice, the proximal port 110 and distal port 120 of medical valve 10 should be cleaned (e.g., swabbed) prior to any connection and after any disconnection. After properly swabbing the distal port 120 of the medical valve 10, a medical practitioner 20 connects the medical valve 10 to the patient 30 (step 710). To do so, the medical practitioner 20 may connect the distal port 120 of the medical valve 10 to the catheter 70, which terminates at a needle inserted into the patient 30 (see FIG. 1).

After connecting the valve 10 to the patient 30, the medical practitioner 20 swabs the valve proximal port 110 and inserts the medical instrument 40 into the proximal port 110 (step 720). Connection and insertion of the medical instrument 40 creates a positive displacement at the distal port 120 of the medical valve 10. As the medical practitioner 20 moves the medical instrument distally (step 730) into the medical valve 10, the tip of the instrument 40 slides along the proximally exposed surface 200 of the rotating member 180 to rotate the rotating member 180. The rotating member 180 continues to rotate until the member channel 220 is in fluid communication with the fluid path 290. At this point, the proximal port 110 and distal port 120 are also in fluid communication, and the valve 10 is open.

As noted above, the valve 10 requires a relatively low prime volume because medical instruments 40 used to open the medical valve 10 take up most of the volume within the medical valve 10 (see FIGS. 4A to 4G). Additionally, because the disconnect and valve closing time is short, a vacuum may be formed in the void volume when the medical instrument 40 is disconnected.

Once the valve 10 is open and the proximal port 110 and distal port 120 are in fluid communication, the medical practitioner 20 can transfer fluids to or from the patient (step 740). For example, if the medical practitioner 20 wishes to administer a medication to the patient 30, he/she may depress the syringe plunger and transfer the medication into the patient 30. Alternatively, the medical practitioner 20 may withdraw blood from the patient 30.

After completing the fluid transfer(s), the medical practitioner 20 can remove the medical instrument (step 750). As discussed above, the medical practitioner 20 should take care not to squeeze the sides of the syringe or medical instrument 40. Doing so may create a positive or negative displacement at the distal port 120 of the medical valve 10. If done properly, removal of the medical instrument 40 should result in a substantially neutral displacement at the valve distal port 120.

As discussed above with reference to FIGS. 4A to 4G, the rotating member 180 will begin to rotate back toward the closed position as the medical practitioner 30 withdraws the medical instrument 40 from the medical valve 10.

Only a small amount of rotation is required to fully close the valve 10, although the rotating member 180 will continue to rotate back to the rest position shown in FIG. 4A.

It should be noted that the above embodiments describe a medical valve 10 in which the proximal port 110 and the distal port 120 are aligned with one another. However, in various other embodiments of the present invention, the medical valve 10 can include a Y-site branch 100A (e.g., see FIG. 2B). The Y-site branch 100A may extend from the housing 100 to form a Y-site channel. The Y-site channel may be in fluid communication with the valve distal port 120. To ensure sterility, the Y-site channel may have a resilient diaphragm, or a valve of some type. Alternatively, the Y-site channel may have no valving means.

It is also important to note that the embodiments discussed above refer to the use of the medical valve 10 in patient or hospital type setting. However, the medical valve 10 can also be used in the bio-pharmaceutical industry or other non-patient setting. For example, a technician 20 can use valve 10 as an injection or aspiration site in a bio-pharmaceutical manufacturing or R&D process.

In addition, as noted above, although most of the embodiments above describe a rotating member 180 made from a rigid material and a internal gland 230 made from a resilient or elastomeric material, the material characteristics may be reversed. For instance, the rotating member 180 can be a resilient material while the gland may be a rigid material. In such embodiments, the valve operation will be very similar in many respects, but complimentary to that discussed. For example, the interaction between the wings 210 and the mating surface 250 on the internal gland 230 differ. Specifically, instead of the rigid wings 210 deforming the elastomeric gland material into the recesses 310, the rigid gland material will deform the elastomeric wings. However, the gland will still bias the valve 10 toward the closed position. The deformation of the wings 210 will create the spring force, rather than the gland material deformation.

Figure 8A:
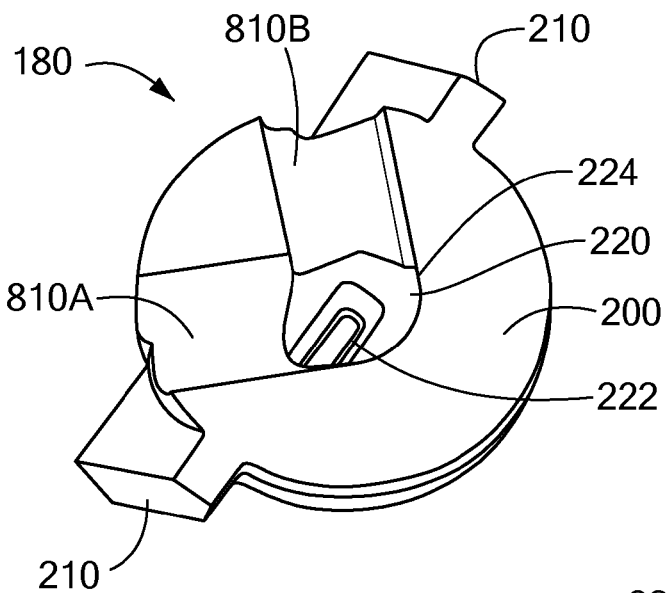
FIGS. 8A to 8C schematically show alternative embodiments of the rotating member within the valve of FIG. 2A.
Figure 8B:
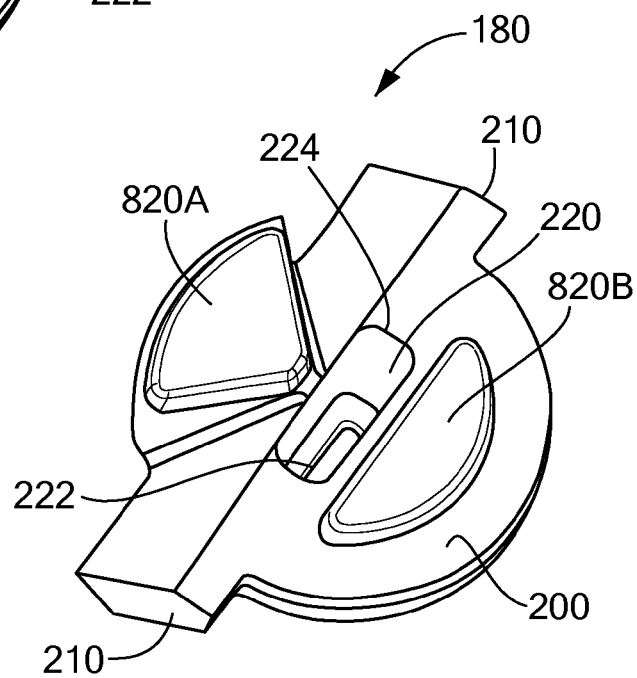
Figure 8C:
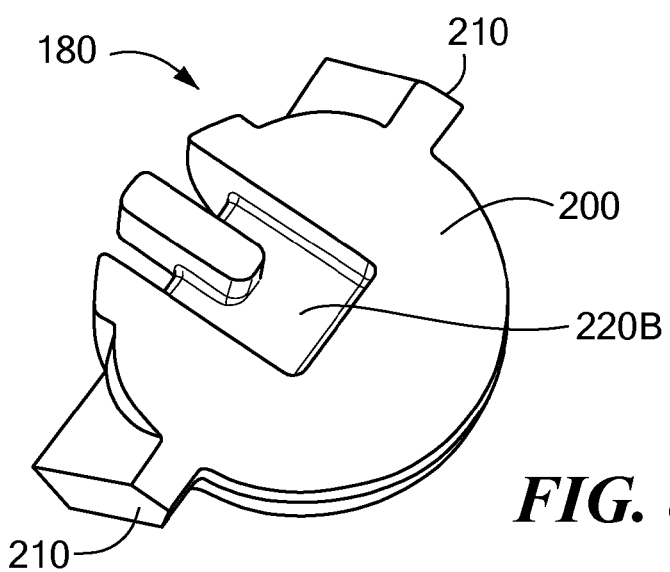

FIGS. 8A to 8C show alternative embodiments of the rotating member 180. As mentioned above and as shown in FIG. 8A, the rotating member 180 may have grooves 810A and 810B (FIG. 8A) to improve flushing and/or for directing fluid toward the inlet 224 of the member channel 220. Among other ways, the channels may extend radially outwardly from the center of the proximally exposed surface 200.

As shown in FIG. 8B, the rotating member 180 may also have protrusions 820A and 820B extending out from the proximally exposed surface 200. The protrusions may be any number of sizes and/or shapes and may be located in a variety of places on the proximally exposed surface 200. For example, as shown in FIG. 8B, the rotating member 180 may have a triangular shaped protrusion 820A located on one side of the member channel 220 and a hemispherical shaped protrusion 820B located on the other side of the member channel 220.

As shown in FIG. 8C, in some embodiments, the member channel 220 does not pass through the rotating member 180. Instead, the rotating member 180 may have a member channel 220B that extends between the proximally exposed surface 200 and the hemispherical surface 180 along the outer surface of the rotating member 180.

Figure 9A:
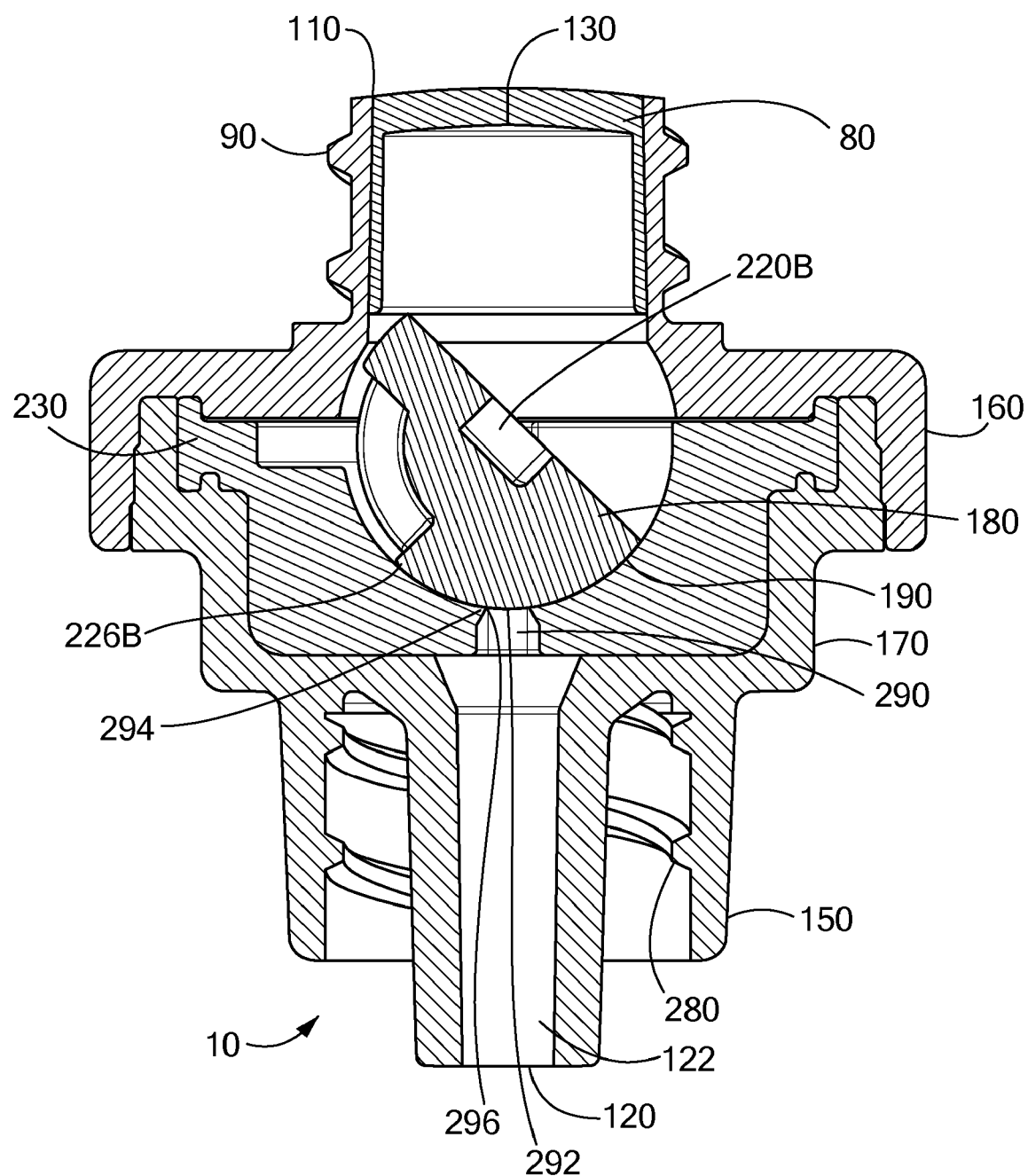
FIGS. 9A and 9B schematically show cross-sectional views an alternative embodiment the alternative rotating member shown in FIG. 8C. These figures show the valve in the open and closed modes.
Figure 9B:
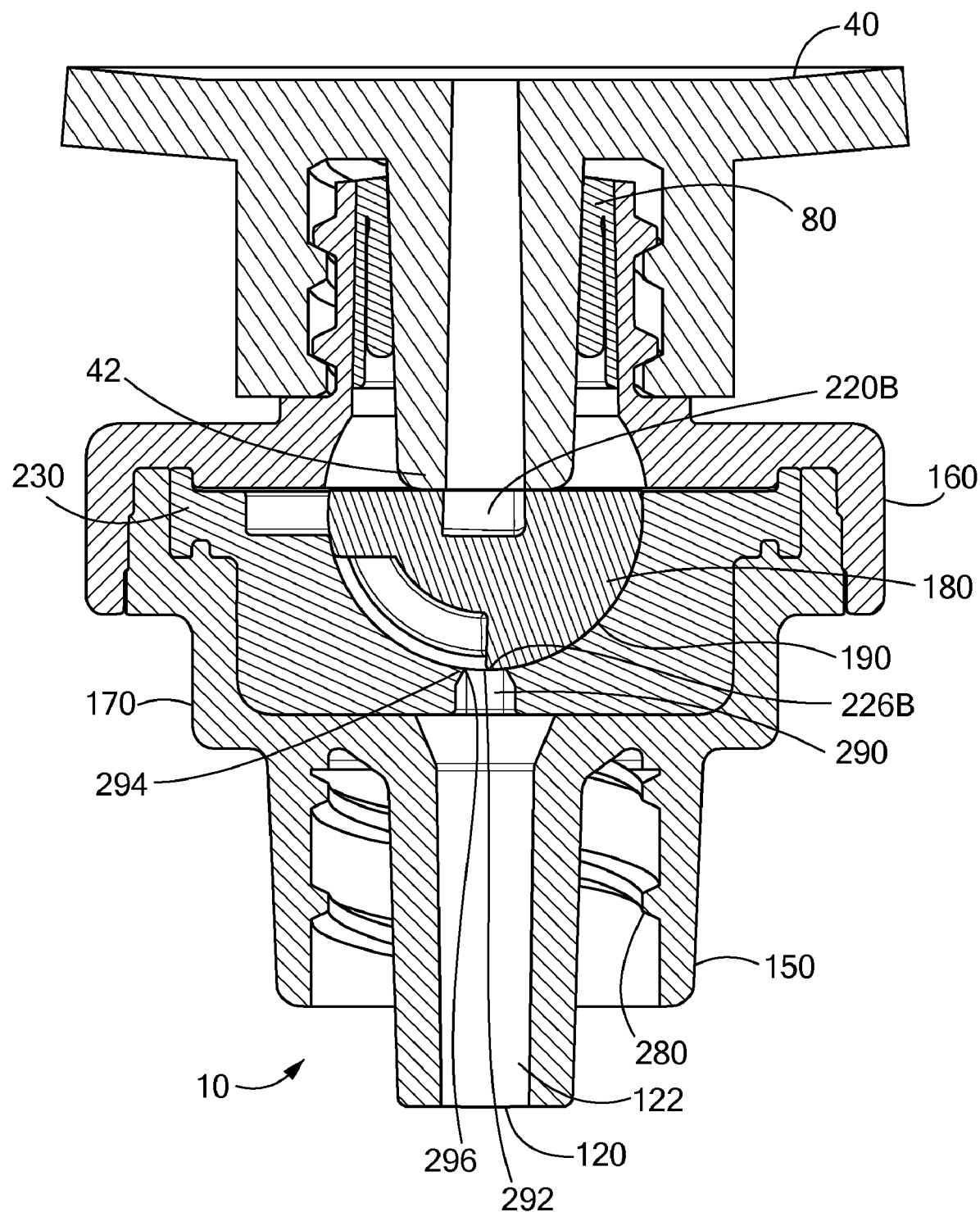

FIGS. 9A and 9B show a cross sectional view of the medical valve 10 with the rotational member shown in FIG. 8C. FIG. 9A shows the medical valve 10 in the closed mode, and FIG. 9B shows the medical valve 10 in the open mode. The operation of this embodiment of the valve 10 is substantially similar to the operation described above. The leading edge 226B of member channel 220B passes the first edge 296 of the fluid path 290, thus causing the valve 10 to open. As with some other embodiments, only a small amount of rotation is required to transition the valve back to the closed mode (e.g., only a small amount of rotation is required to fluidly disconnect the leading edge 226B of the member channel 220B from the fluid path 290). Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow, and a closed mode that prevents fluid flow, the medical valve comprising:
   a housing having an inlet and an outlet;
   a movable member with a member channel therethrough, the movable member being movable to cause the valve to transition from the closed mode to the open mode after insertion of a medical implement into the inlet, the member channel fluidly communicating the inlet and the outlet when in the open mode; and
   a resilient member having a member flow path in fluid communication with the outlet, the movable member sliding along the resilient member when transitioning between the open mode and the closed mode,
   the resilient member normally having a flange about the member flow path, the movable member compressing the flange, the flange fluidly disconnecting the member flow path from the member channel when in the closed mode, wherein the flange normally overhangs the member flow path.

2. The medical valve as defined by claim 1 wherein the member channel has a distal opening, the flange being generally about the distal opening when in the open mode.

3. The medical valve as defined by claim 2 wherein the flange generally seals about the distal opening when in the open mode.

4. The medical valve as defined by claim 1 wherein the movable member is a rotational member.

5. The medical valve as defined by claim 1 wherein the movable member compresses the flange to have a surface with a contour that generally is complimentary with the contour of the portion of the movable member contacting the flange.

6. The medical valve as defined by claim 1 wherein the flange wipes against the movable member to effectively form a wiper seal.

7. The medical valve as defined by claim 1 wherein the movable member compresses the flange the entire time the valve transitions between the open and closed modes.

8. The medical valve as defined by claim 1 wherein the resilient member comprises silicone.

9. The medical valve as defined by claim 1 wherein the member channel has a distal opening and the valve has a partially open mode, the distal opening being between first and second portions of the flange when in the partially open mode, the first portion extending across the distal opening when in the partially open mode, the second portion of the flange being radially outward of the distal opening when in the partially open mode.

10. A medical valve having an open mode that permits fluid flow, and a closed mode that prevents fluid flow, the medical valve comprising:
    a housing having an inlet and an outlet;
    a movable member with a member channel therethrough, the movable member being movable to cause the valve to transition from the closed mode to the open mode after insertion of a medical implement into the inlet, the member channel fluidly communicating the inlet and the outlet when in the open mode; and
    a resilient member having a member flow path with a proximal opening, the resilient member also having a flange about the proximal opening of the member flow path, the flange sealing the proximal opening in the closed mode and normally overhanging the proximal opening of the member flow path.

11. The medical valve as defined by claim 10 wherein the member flow path has a distal end and an interior part between the proximal opening and the distal end, the member flow path having an inner dimension that increases in size from the proximal opening to the interior part.

12. The medical valve as defined by claim 10 wherein the movable member compresses the flange to a contour that generally corresponds to the contour of the portion of the movable member contacting the flange.

13. The medical valve as defined by claim 10 wherein the flange fluidly disconnects the member flow path from the member channel when in the closed mode.

14. The medical valve as defined by claim 10 wherein the member channel has a distal opening, the flange being generally about the distal opening when in the open mode.

15. The medical valve as defined by claim 14 wherein the flange generally seals about the distal opening when in the open mode.

16. The medical valve as defined by claim 10 wherein the movable member is a rotational member.

17. The medical valve as defined by claim 10 wherein the resilient member supports the movable member.

18. The medical valve as defined by claim 10 wherein the movable member compresses the flange in the closed mode to seal the proximal opening.

19. A medical valve having an open mode that permits fluid flow, and a closed mode that prevents fluid flow, the medical valve comprising:

a housing having an inlet and an outlet;

movable means with a member channel therethrough, the movable means being movable to cause the valve to transition from the closed mode to the open mode after insertion of a medical implement into the inlet, the member channel fluidly communicating the inlet and the outlet when in the open mode; and a resilient member having a member flow path in fluid communication with the outlet, the movable means sliding along the resilient member when transitioning between the open mode and the closed mode, the resilient member normally having a means for sealing about the member flow path, the movable means compressing the sealing means, the sealing means fluidly disconnecting the member flow path from the member channel when in the closed mode, wherein the sealing means is a flange that normally overhangs the member flow channel.

20. The medical valve as defined by claim 19 wherein the movable means comprises a rotating member.

21. The medical valve as defined by claim 19 wherein the sealing means forms a proximal opening of the member flow path, the proximal opening having a perimeter, the sealing means sealing the perimeter of the proximal opening in both the open and closed modes.

22. The medical valve as defined by claim 1 wherein the resilient member normally biases the moveable member to close the valve.

23. The medical valve as defined by claim 1, wherein the flange normally protrudes upwardly from a surface of the resilient member.

24. The medical valve as defined by claim 1, wherein the resilient member defines a concavity, the flange protruding into the cavity.

25. The medical valve as defined by claim 1, the flange narrows the opening to the member flowpath.

26. The medical valve as defined by claim 1, wherein the resilient member is elastomeric.

27. A medical valve having an open mode that permits fluid flow, and a closed mode that prevents fluid flow, the medical valve comprising:

a housing having an inlet and an outlet;

a rotatable member with a member channel therethrough, the rotatable member being rotatable to cause the valve to transition from the closed mode to the open mode after insertion of a medical implement into the inlet, the member channel fluidly communicating the inlet and the outlet when in the open mode; and a resilient member defining a concavity and supporting the rotatable member, the resilient member having a member flow path in fluid communication with the outlet, the rotatable member sliding along a concave surface of the concavity when transitioning between the open mode and the closed mode, the resilient member normally having a flange about the member flow path, the flange normally protruding proximal from the concave surface and overhanging the member flow path, the rotatable member compressing the flange, the flange fluidly disconnecting the member flow path from the member channel when in the closed mode.

* * * * *